US008423167B2

(12) United States Patent
Sanders et al.

(10) Patent No.: US 8,423,167 B2
(45) Date of Patent: Apr. 16, 2013

(54) COMPUTER AIDED DESIGN AND MANUFACTURING OF TRANSTIBIAL PROSTHETIC SOCKETS

(75) Inventors: Joan E. Sanders, Sammamish, WA (US); Michael R. Severance, Seattle, WA (US); Timothy R. Myers, Seattle, WA (US); George Turkiyyah, Seattle, WA (US); Elizabeth A. Sorenson, Ramona, CA (US); Ellen L. Lee, Corvallis, OR (US)

(73) Assignee: University of Washington, Seattle, WA (US)

( * ) Notice: Subject to any disclaimer, the term of this patent is extended or adjusted under 35 U.S.C. 154(b) by 644 days.

(21) Appl. No.: 12/507,560

(22) Filed: Jul. 22, 2009

(65) Prior Publication Data

US 2010/0023149 A1 Jan. 28, 2010

Related U.S. Application Data

(60) Provisional application No. 61/083,479, filed on Jul. 24, 2008.

(51) Int. Cl.
*G06F 17/50* (2006.01)
*G06F 19/00* (2011.01)

(52) U.S. Cl.
USPC ............ 700/98; 700/118; 700/161; 700/195; 623/901; 703/1

(58) Field of Classification Search .................... 700/98, 700/109, 110, 118, 119, 161, 163, 195; 703/1; 623/901
See application file for complete search history.

(56) References Cited

U.S. PATENT DOCUMENTS

| 5,280,429 A | | 1/1994 | Withers .................. 364/413.15 |
|---|---|---|---|
| 5,539,649 A | * | 7/1996 | Walsh et al. .................. 623/901 |
| 6,125,297 A | | 9/2000 | Siconolfi ....................... 600/547 |
| 6,151,523 A | | 11/2000 | Rosell Ferrer et al. ....... 600/547 |
| 6,463,351 B1 | * | 10/2002 | Clynch ......................... 700/163 |
| 6,690,181 B1 | | 2/2004 | Dowdeswell et al. ......... 324/691 |
| 6,927,858 B2 | | 8/2005 | Boone et al. .................. 356/437 |

(Continued)

OTHER PUBLICATIONS

Rogers et al. "Advanced trans-tibial socket fabrication using selective laser sintering" Prsthetics and Orthotics International Mar. 2007 31(1) pp. 88-100.*

(Continued)

*Primary Examiner* — Kavita Padmanabhan
*Assistant Examiner* — Steven Garland
(74) *Attorney, Agent, or Firm* — Kilpatrick Townsend and Stockton LLP

(57) ABSTRACT

For use in connection with evaluating prosthetic sockets (and other objects) designed and fabricated with computer aided design and manufacturing software, the shape of a socket is accurately scanned and digitized. The scanned data are then compared to either an electronic shape data file, or to the shape of another socket, a positive model of a residual limb (or socket), or a residual limb. Differences detected during the comparison can then be applied to revise the design or fabrication of the socket, to more accurately achieve a desired shape that properly fits the residual limb of a patient and can be used to solve the inverse problem by correcting for observed errors of a specific fabricator before a socket is produced. The digitizing process is implemented using a stylus ball that contacts a surface of the socket to produce data indicating the three-dimensional shape of the socket.

25 Claims, 10 Drawing Sheets

U.S. PATENT DOCUMENTS

| | | | |
|---|---|---|---|
| 7,150,762 B2 | 12/2006 | Caspers | 623/27 |
| 7,310,999 B2 | 12/2007 | Miller | 73/149 |
| 7,794,505 B2 | 9/2010 | Clausen et al. | 623/50 |
| 2008/0200994 A1 | 8/2008 | Colgate et al. | 623/24 |

OTHER PUBLICATIONS

Sanders et al., "A digitizer with exceptional accuracy for use in prosthetic research: A technical note", Journal of Rehabilitation Research and Development, vol. 40, No. 2; Mar./Apr. 2003; pp. 191-196.

Sanders et al., "CAD/CAM transtibial prosthetic sockets from central fabrication facilities: How accurate are they?", Journal of Rehabilitation Research and Development, vol. 44, No. 3; 2007; pp. 395-406.

Zachariah et al., "A Method for Aligning Trans-Tibial Residual Limb Shapes so as to Identify Regions of Shape Change", IEEE Transactions on Neural Systems and Rehabilitation Engineering, vol. 13, No. 4; Dec. 2005; pp. 551-557.

Cotton et al., "A Novel Thick-Film Piezoelectric Slip Sensor for a Prosthetic Hand." *IEEE Sensors Journal*, vol. 7, No. 5: 752-761, May 2007.

Boone et al., "Automated fabrication of mobility aids: Review of the AFMA process and VA/Seattle ShapeMaker software design." *Journal of Rehabilitation Research and Development* vol. 31, No. 1: 42-49, 1994.

Boone et al., "Automated Fabrication of Mobility Aids: Clinical Demonstration of the UCL Computer Aided Socket Design System," *Journal of Prosthetics and Orthotics* vol. 1, No. 3: 187-190, 1989.

Chan et al., "Dynamic Rectification: A Statistically Based Evolving Socket Rectification Mechanism." *7th World Congress of the International Society for Prosthetics and Orthotics* Chicago, IL: 27, Jun. 28-Jul. 3, 1992.

Chan et al., "Surface Curvature Analysis for Enhanced Computer-Aided-Design of Prosthetic Sockets." *IEEE* 1292-1293, 1993.

Commean et al., "Design of a 3-D surface scanner for lower limb prosthetics: A technical note." *Journal of Rehabilitation Research and Development* vol. 33, No. 2: 267-278, 1996.

Convery et al., "Measurement of the consistency of patellar-tendon-bearing cast rectification." *Prosthetics and Orthotics International* vol. 27, No. 3: 207-213, 2003.

Dean et al., "A Software Package for Design and Manufacture of Prosthetic Sockets for Transtibial Amputees," *IEEE Transactions on Biomedical Engineering* vol. 32, No. 4: 257-262, 1985.

Hastings et al., "Frequency Content of Prosthetic and Orthotic Shapes: A Requirement for CAD/CAM Digitizer Performance." *Journal of Prosthetics and Orthotics* vol. 10, No. 1: 2-6, 1998.

He et al., "Test of a vertical scan mode in 3-D imaging of residual limbs using ultrasound." *Journal of Rehabilitation Research and Development* vol. 36, No. 2: 14pp., 1999.

Houston et al., "Automated fabrication of mobility aids (AFMA): Below-knee CASD/CAM testing and evaluation program results." *Journal of Rehabilitation Research and Development* vol. 29, No. 4: 78-124, 1992.

Houston et al., "The VA-Cyberware lower limb prosthetics-orthotics optical laser digitizer." *Journal of Rehabilitation Research and Development* vol. 32. No. 1: 55-73, 1995.

Johansson et al., "Accuracy and precision of volumetric determinations using two commercial CAD systems for prosthetics: A technical note." *Journal of Rehabilitation Research and Development* vol. 35, No. 1: 27-33, 1998.

Krouskop et al., "Measuring the shape and volume of an above-knee stump." *Prosthetics and Orthotics International* vol. 12, No. 3: 136-142, 1988.

Kulczycka et al., "Qualitative and quantitative comparisons of B-spline offset surface approximation method." *Computer-Aided Design* vol. 34: 19-26, 2002.

Lemaire, E., "A CAD analysis programme for prosthetics and orthotics." *Prosthetics and Orthotics International* vol. 18, No. 2: 112-117, 1994.

Lemaire et al., "A Quantitative Method for Comparing and Evaluating Manual Prosthetic Socket Modifications." *IEEE Transactions on Rehabilitation Engineering* vol. 4, No. 4: 303-309, 1996.

Lemaire et al., "Validation of a quantitative method for defining CAD/CAM socket modifications." *Prosthetics and Orthotics International* vol. 23, No. 1: 30-44, 1999.

Lilja et al., "Proper Time for Definitive Transtibial Prosthetic Fitting." *Journal of Prosthetics and Orthotics* vol. 9, No. 2: 90-95, 1997.

Lilja et al., "Volumetric determinations with CAD/CAM in prosthetics and orthotics: Error of measurement." *Journal of Rehabilitation Research and Development* vol. 32, No. 2: 141-148, 1995.

McGarry et al., "Evaluation of a contemporary CAD/CAM system." *Prosthetics and Orthotics International* vol. 29, No. 3: 221-229, 2005.

McGarry et al., "Evaluation of the effect of shape on a contemporary CAD system." *Prosthetics and Orthotics International* vol. 32, No. 2: 145-154, 2008.

Sidles et al., "A quantitative comparison of amputee stump and socket shapes." *Proceedings of the 35th Annual Meeting—Orthopaedic Research Society* Las Vegas, NV: Feb. 1989.

Sidles et al., "Mathematical techniques for comparing residual limb and sockate shapes." *Proceedings of the ISPO Sixth World Congress* Kobe, Japan: Nov. 1989.

Sidles et al., "Rectification Maps: A New Method for Describing Residual Limb and Socket Shapes." *Journal of Prosthetics and Orthotics* vol. 1, No. 3: 149-153, 1989.

Sidles et al., "Rectification Maps: A New Method for Describing Stump and Socket Shapes." In: Davies et al., eds. *Report of the ISPO Workshop on CAD/CAM in Prosthetics and Orthotics* Seattle, WA; Copenhagen, Denmark; International Society of Prosthotists and Orthotists: 15-18, 1988, 1990.

Smith et al., "Validation of spiral CT and optical surface scanning for lower limb stump volumetry." *Prosthetics and Orthotics International* vol. 19, No. 2: 97-107, 1995.

Torres-Moreno et al., "A reference shape library for computer aided socket design in above-knee prostheses." *Prosthetics and Orthotics International* vol. 13, No. 3: 130-139, 1989.

Travis et al., "Computer-aided socket design for trans-femoral amputees." *Prosthetics and Orthotics International* vol. 17, No. 3: 172-179, 1993.

Vannier et al., "Three-Dimensional Lower-Extremity Residua Measurement Systems Error Analysis." *Journal of Prosthetics and Orthotics* vol. 9, No. 2: 67-76, 1997.

Walsh et al., "A Computerized System to Manufacture Prostheses for Amputees in Developing Countries." *Journal of Prosthetics and Orthotics* vol. 1, No. 3: 165-181, 1989.

Armstrong et al., "Bioimpedance spectroscopy technique: Intra-, extracellular, and total body water." *Medicine & Science in Sports & Exercise* vol. 29(12): 1657-1663, 1997.

Cole et al., "Electrical analogues for tissues." *Experimental Neurology* vol. 24(3): 459-473, 1969.

De Lorenzo et al., "Predicting body cell mass with bioimpedance by using theoretical methods: a technological review." *Journal of Applied Physiology* vol. 82 (5): 1542-1558, 1997.

Donadio et al., "Estimate of body water compartments and of body composition in maintenance hemodialysis patients: Comparison of single and multifrequency bioimpedance analysis." *Journal of Renal Nutrition* vol. 15, No. 3: 332-344, 2005.

Fenech et al., "Extracellular and intracellular volume variations during postural change measured by segmental and wrist-ankle bioimpedance spectroscopy." *IEEE Transactions on Biomedical Engineering* vol. 51, No. 1: 166-175, 2004.

Fuller et al., "Predicting composition of leg sections with anthropometry and bioelectrical impedance analysis, using magnetic resonance imaging as reference." *Clinical Science* London; vol. 96(6): 647-657, 1999.

Gilbert et al., "Effect of frequency, circuit analysis and instrument on extracellular and total body resistance." *Medicine & Science in Sports & Exercise* 672 Suppl: S118, 1995.

Hanai T., "Electrical Properties of Emulsions." In: Sherman P, editor. *Emulsion Science* London, England, Academic Press: 354-477, 1968.

Hoffer et al., "Correlation of whole-body impedance with total body water volume." *Journal of Applied Physiology* vol. 27, No. 4: 531-534, 1969.

Matthie et al., "Analytic assessment of the various bioimpedance methods used to estimate body water." *Journal of Applied Physiology* vol. 84(5): 1801-1816, 1998.

Nyboer J., "Workable volume and flow concepts of biosegments by electrical impedance plethysmography." *T.I.T Journal of Life Sciences* vol. 2(1): 1-13, 1972; Reprinted in *Nutrition* vol. 7, No. 6: 396-408, 1991.

Organ et al., "Segmental bioelectrical impedance analysis: Theory and application of a new technique." *Journal of Applied Physiology* vol. 77(1): 98-112, 1994.

Salinari et al., "Bioimpedance analysis: A useful technique for assessing appendicular lean soft tissue mass and distribution." *Journal of Applied Physiology* vol. 94(4): 1552-1556, 2003.

Sanders et al., "Assessment of residual-limb volume change using bioimpedance." *Journal of Rehabilitation Research & Development* vol. 44, No. 4: 525-536. 2007.

Sanders et al., "Bioimpedance Analysis and Diurnal Volume Change: Assessment on Trans-Tibial Amputee Prosthesis Users." *Archives of Physical Medicine and Rehabilitation* pp. 1-22, submitted 2008.

Sanders et al., "Clinical utility of in-socket residual limb volume change measurement: Case study results." *Prosthetics and Orthotics International* pp. 1-29, submitted 2009.

Segal et al., "Estimation of extracellular and total body water by multiple-frequency bioelectrical-impedance measurement." *The American Journal of Clinical Nutrition* vol. 54(1): 26-29, 1991.

Siconolfi et al., "Assessing total body and extracellular water from bioelectrical response spectroscopy." *Journal of Applied Physiology* vol. 82(2): 704-710, 1997.

Thomas et al., "A comparison of segmental and wrist-to-ankle methodologies of bioimpedance analysis." *Applied Radiation Isotopes* vol. 49, No. 5/6: 477-78, 1998.

Van Loan et al., "Use of bioimpedance spectroscopy to determine extracellular fluid, intracellular fluid, total body water, and fat-free mass." *Human Body Composition: in vivo Methods, Models, and Assessment* Edited by: Ellis, New York: 67-70, 1993.

Wotton et al., "Comparison of whole body and segmental bioimpedance methodologies for estimating total body water." *Annals New York Academy of Sciences* 904: 181-186, 2000.

Zachariah et al., "Shape and volume change in the transtibial residuum over the short term: Preliminary investigation of six subjects." *Journal of Rehabilitation Research & Development* vol. 41, No. 5: 683-694, 2004.

Zhu et al., "Dynamics of segmental extracellular volumes during changes in body position by bioimpedance analysis." *Journal of Applied Physiology* vol. 85(2): 497-504, 1998.

Zhu et al., "Methods and reproducibility of measurement of resistivity in the calf using regional bioimpedance analysis." *Blood Purification* vol. 21: 131-136, 2003.

Zhu et al., "Validation of changes in extracellular volume measured during hemodialysis using a segmental bioimpedance technique." *ASAIO Journal* vol. 44(5): M541-545, 1998.

Chaudhari et al., "Hyperspectral and multispectral bioluminescence optical tomography for small animal imaging." *Physics in Medicine and Biology* vol. 50, No. 23: 5421-5441, Dec. 7, 2005.

Meijer et al., "Method for the measurement of susceptibility to decubitus ulcer formation." *Medical & Biological Engineering & Computing* vol. 27(5): 502-506, 1989.

Meijer et al. "Susceptibility to decubitus ulcer formation." *Archives of Physical Medicine and Rehabilitation* vol. 75(3): 318-323, 1994.

Mein et al., "Skin temperature response to a pressure load: studies in subjects before and during spinal anethesia." *Archives of Physical Medicine and Rehabilitation* vol. 76(3): 243-245, 1995.

Sanders, J.E., "Thermal response of skin to cyclic pressure and pressure with shear: a technical note." *Journal of Rehabilitation Research and Development* vol. 37, No. 5: 511-515, 2000.

van Marum et al., "Impaired blood flow response following pressure load in diabetic patients with cardiac autonomic neuropathy." *Archives of Physical Medicine and Rehabilitation* vol. 78(9): 1003-1006, 1997.

van Marum et al., "Relationship between internal risk factors for development of decubitus ulcers and the blood flow response following pressure load." *Angiology* vol. 52(6): 409-416, 2001.

van Marum et al., "The relationship between pressure ulcers and skin blood flow response after a local cold provocation." *Archives of Physical Medicine and Rehabilitation* vol. 83(1): 40-43, 2002.

\* cited by examiner

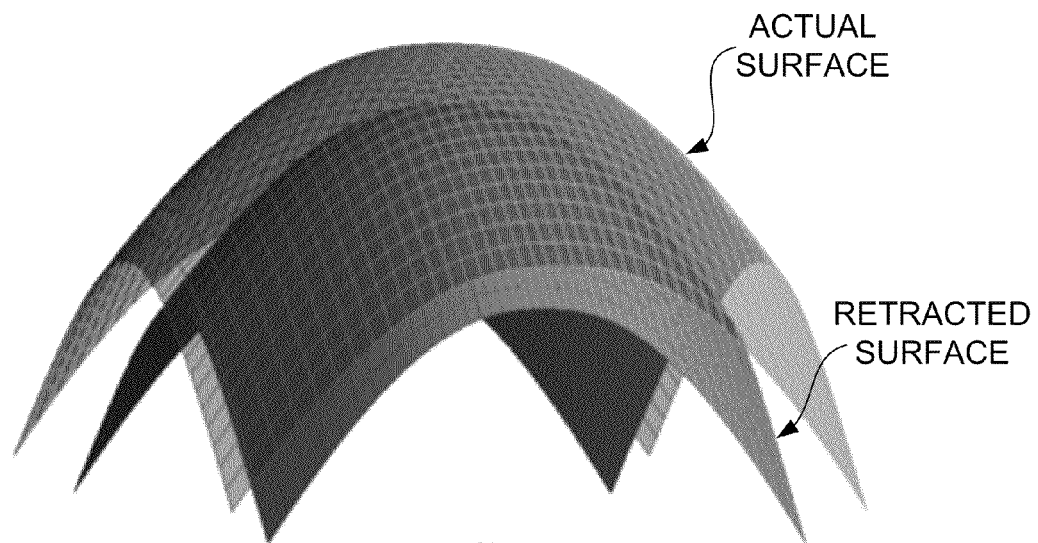
FIG. 8
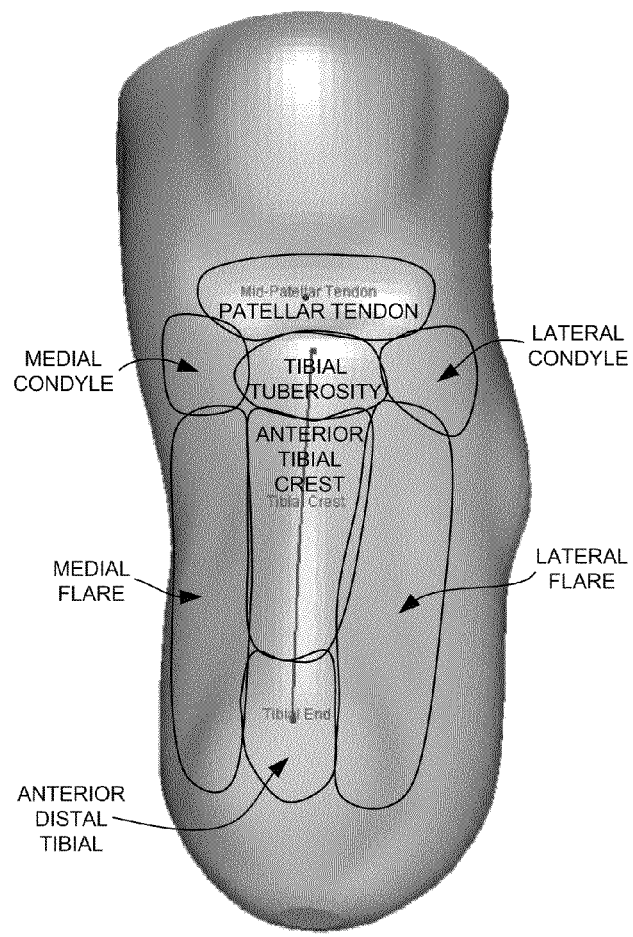
FIG. 9A ANTERIOR VIEW

FIG. 9D MEDIAL VIEW

FIG. 9C LATERAL VIEW

FIG. 9B POSTERIOR VIEW

COMPUTER AIDED DESIGN AND MANUFACTURING OF TRANSTIBIAL PROSTHETIC SOCKETS

RELATED APPLICATIONS

This application is based on a prior provisional application, Ser. No. 61/083,479, filed on Jul. 24, 2008, the benefit of the filing date of which is hereby claimed under 35 U.S.C. §119(e).

GOVERNMENT RIGHTS

This invention was made with government support under R01-EB004329 awarded by National Institutes of Health (NIH)-Federal Reporting. The government has certain rights in the invention.

BACKGROUND

There are approximately 84,500 to 114,000 new lower-limb amputations each year in the U.S. Amputation rates are rising each year, in part because of the rapid increase in diabetes and also because of an improvement in treating traumatic injury and vascular disease. More of the patients experiencing these problems are able to live longer but require a limb amputation to survive. Further, the recent wars in Iraq and Afghanistan have caused an increase in the number of servicemen and women who undergo an amputation, typically young individuals who are otherwise healthy. Because of the early age at which the amputation occurred, these individuals will be prosthesis users for many years. Thus, there is a strong need to create quality prosthetic limbs for the increasing lower-limb amputee population.

The design of an effective prosthetic socket is crucial to the rehabilitation and overall health of a person with an amputated limb. This point cannot be overemphasized. Most of the time and energy a practitioner applies in making a prosthesis is spent on fabricating the socket that must be fitted to the residual limb. The prosthetic socket must be shaped so that it supports the residual limb in load tolerant areas, while avoiding irritation of sensitive regions on the limb that contact the inner surface of the socket. If these criteria are not achieved, when the patient uses the prosthesis, residual limb soft tissue breakdown often occurs. The result is painful sores, blisters, ulcers, or cysts on the residual limb that typically restrict continued prosthesis use, and in severe cases, necessitate a further amputation to a higher anatomical level, which can lead to further disability. The incidence of skin breakdown in lower-limb amputees has been reported to be from 24% to 41%. Accordingly, at any one time, as many as 41% of prosthesis users may be experiencing breakdown of the tissue on the residual limb. The principle cause of such breakdown is a poorly fitting prosthetic socket.

Practitioners face challenges in making quality sockets for the increasing amputee population. Also, there is a shortage of prosthetists in the industry, and that shortage is expected to increase in the future, as the demand for prosthetic devices increases. A prosthetist's time is precious and must be used as efficiently as possible. It will therefore be evident that there is a need for technology to improve a prosthetist's efficiency, speed, documentation, repeatability, and quality of fitting a socket to a patient's residual limb, and to ensure a proper socket design early in the process of fitting a prosthetic socket to a recipient.

Modern prostheses are often made using computer-aided-design and computer-aided-manufacturing (CAD/CAM) methods, which were introduced to the prosthetics field about 25 years ago to address these needs. When using a CAD/CAM approach to produce a fitted socket, a practitioner measures the shape of the residual limb using either a cast impression or a commercially-available scanning device that implements one of a number of shape acquisition modalities (e.g., use of a laser scanner, contact hand digitizer, video scanner, structured light projection, or digitization of a plaster cast). The practitioner then designs a socket on a computer using one of several commercially available software packages. As shown in FIG. 1A, a design 22 can be viewed on a monitor 20 and modified as desired using input provided via a keyboard 24 or a mouse or other pointing device 22. As shown in FIG. 1B, the resulting shape is then sent electronically to a custom computer numerical control (CNC) mill 32, referred to in the art as a "carver," to fabricate a positive model 34 as a block of material used for the model is rotated on an indexing table 30. This positive model is used to form the socket. For example, a thermoformer can be used to vacuum form a socket by heating a polymer cone and then vacuum forming it onto the positive model. Alternatively, a thermoplastic sheet 40 can be draped or wrapped over the positive model, as shown in a FIG. 1C. After the edges are trimmed, a completed socket 50 is provided, as shown in FIG. 1D.

Other methods for socket fabrication exist, including a novel motion guided extrusion technique (referred to as SQUIRT SHAPE™, developed at Northwestern University), and other rapid prototyping techniques. However, regardless of the method used for fabricating a socket, there is often a quality control problem that arises in the fabrication process, and means are needed to enable a prosthetic socket designer to determine if the fabricated socket indeed accurately matches the shape that was designed. Currently, practitioners creating sockets often spend too much time fixing or remaking the sockets that were produced incorrectly by the CAD/CAM process—where the errors typically arise either during the carving process or the forming process, or both. The benefits of CAD/CAM, which include improved efficiency, speed, documentation, and lower expense, are substantially reduced or even lost because of this problem. Prosthetists who have an in-office CAD/CAM system suite, central fabrication facilities, and manufacturers of CAD/CAM equipment used to produce sockets could thus clearly benefit from a new technology for evaluating the quality of each socket produced, to avoid the expense and delay incurred to fix or remake a socket as necessary to achieve a proper fit with the patient's residual limb.

For example, after making a socket, it would be desirable for a prosthetist to be able to place the socket in a device that can assess its shape and compare it with an electronic data file for the socket that was created using a CAD/CAM system. Such files define a desired shape for the socket and are stored on a computer hard drive and used for carving the socket positive model. The shape quality information relating to the match between the socket and the design file could then be presented to the prosthetist on the computer, using charts and images. The device might then indicate very clearly where modification is needed if the socket is not properly shaped. The practitioner could decide if the socket is acceptable, if it should be modified, or if a new socket should be made—all before attempting to fit the socket to the patient's residual limb. Having such information would potentially save a tremendous amount of time when fabricating sockets using a CAD/CAM system, by avoiding the need to bring the patient back to test fit a socket, determining that a problem exists, making adjustments, and then having the patient come in once again to repeat the process. Thus, such a device and system might save time and money and reduce pain to the patient.

A system to provide this functionality would require both hardware and software. The hardware would enable very precise shape measurements of the interior of a socket, for example, by using a contact stylus to measure the shape of the socket. The design for a related prior art measurement device was described in a 2003 publication. However, this early measurement device had several problems. Specifically, it was unable to measure areas of the socket with very high curvature. It was also clear that a refinement of the shape reconstruction algorithm was needed so that splines defining the shape of a socket interior might be assembled in r-z planes, rather than r-θ planes, or better, defined as a three-dimensional (3-D) shape. The earlier device also exhibited unacceptable errors and was sensitive to the position of the socket in the device, so that a slight axial misalignment of the measuring device relative to a socket's longitudinal central axis caused an unacceptable error in the evaluation of the socket.

There are a number of other benefits of being able to accurately assess a socket besides simply determining if the socket will properly fit the residual limb of the patient. For example, the data derived from this novel approach and the system that enables it could make it easier to evaluate the changes in a patient's socket design over time, e.g., by comparing a new socket with an old socket, to facilitate patient treatment and creation of a new socket design for the patient. This tool should enable the creation of a database and standards that facilitate substantial improvements in the CAM socket fabrication process. Another application of the tool would be to evaluate different manufacturing equipment and fabricators that are used to produce sockets, evaluate health service providers, and provide information usable by insurance companies.

It would also be desirable to employ such socket measurement hardware and software to determine if the CAD/CAM shaping of the positive model by carving and/or the forming of the socket over the positive model by a socket production facility produces sockets having errors of a consistent nature. By using the hardware and software discussed above to evaluate a plurality of different sockets that have been fabricated by a specific prosthetic facility using CAD/CAM, it should be possible to create an "inverse model" indicating corrections that should be applied by the facility to produce sockets much more closely achieving a desired design and having fewer errors. The corrections would be applied to the desired design file before carving the positive model to ensure that the resulting finished prosthetic socket actually matches the desired design and thus properly fits the residual limb of a patient as intended.

Accordingly, a new approach is needed that addresses these issues by providing an appropriate hardware and software tool or system for assessing the fit of a socket relative to: (a) an electronic shape file for a socket; (b) the shape of another prosthetic socket; (c) the shape of a positive mold of a socket; or, (d) a residual limb shape (e.g., acquired by imaging, contact sensing, or digitizing a cast). This tool should be useful in assessing the fit of sockets produced for both legs and arms, for othoses (i.e., devices that support rather replacing body parts, such as spine orthoses, limb and foot orthoses, and shoe inserts), and for other related tasks.

SUMMARY

This application specifically incorporates herein by reference the disclosure and drawings of the patent application identified above as a related application.

Accordingly, an exemplary method is provided for using a computing device for assessing a prosthetic socket to determine an interior shape of the prosthetic socket and a deviation of the interior shape relative to a shape of a reference. The method includes the step of scanning an interior surface of the prosthetic socket with a stylus ball that remains in contact with the interior surface as a relative position of the stylus ball on the interior surface changes over time. When reconstructing the surface being scanned in two dimensions, the samples of the surface are taken at equal angular intervals rather than during equal time intervals. For two dimensions, the equal angular intervals ensures that the θ values are the same from one scan slice or layer to the next, but use of equal angular intervals is unnecessary when reconstructing the surface being scanned in three dimensions, although it improves the efficiency of the data processing efficiency. The scan produces data indicative of the position of a center of the stylus ball as the point of contact of the ball with the interior surface changes over time. A retracted surface is determined using the computing device, based on the data indicative of the position of the center of the stylus ball over time and the interior surface, by determining control points that define the retracted surface. By projecting outwardly from the points on the retracted surface, along three-dimensional normals from the retracted surface, the method determines offset points used for constructing a three-dimensional surface corresponding to the interior surface of the prosthetic socket. The three-dimensional surface defines the interior shape of the prosthetic socket. Data for the three-dimensional surface of the prosthetic socket defining the shape of the prosthetic socket can then be compared to data defining a shape of the reference, to determine deviations between the shape of the prosthetic socket and the reference. An indication can thus be provided of a magnitude and a location where the shape of the prosthetic socket deviates from the shape of the reference.

The method further includes the step of optimizing the interior surface of the prosthetic socket by projecting inwardly from points on the three-dimensional surface, to intersect with the centers of the stylus ball over time.

The step of comparing the data for the three-dimensional surface of the prosthetic socket to the data defining the shape of the reference can include the step of comparing the data for the three-dimensional surface of the prosthetic socket to data defining a shape of a specific type of reference, such as another prosthetic socket, a residual limb that the prosthetic socket is designed to fit, a positive model of the residual limb that the prosthetic socket is designed to fit, a positive model of the desired prosthetic shaped, or electronically created shape data that represent a desired shape of the prosthetic socket.

Also, the step of comparing the data for the three-dimensional surface of the prosthetic socket to the data defining the shape of the reference can include the step of comparing different regions of the three-dimensional surface of the prosthetic socket to corresponding regions of the reference. The method can further comprise the step of determining both a mean absolute difference and a weighted surface normal difference between the shape of the prosthetic socket and the shape of the reference. Different weightings can be applied to the regions of the prosthetic socket that are compared to the corresponding regions of the reference, wherein the weightings can be based on anatomically related characteristics of the regions or on computed shape features of the regions.

The method can include the step of constructing a B-spline surface by minimizing a sum-of-squares Euclidian distance between measured points corresponding to the centers of the stylus ball, and the interior surface being scanned, at each of a plurality of slices. Successive slices are disposed along a defined axis through the prosthetic socket. The step of constructing a three-dimensional surface corresponding to the interior surface of the prosthetic socket can include the step of implementing a nonlinear optimization to compute the control point locations so as to minimize a Euclidean sum-of-squares distance between the centers of the stylus ball and the B-spline surface.

The method can further include the step of compiling a database comprising a collection of electronic shape file and socket-shape pairs established based on measurements of an interior shape of a plurality of prosthetic sockets produced by a specific socket manufacturing system or source. The data in this database thus relate a measured shape of each of the plurality of prosthetic sockets to a corresponding electronic-shape-file that was used to produce the prosthetic socket. A desired prosthetic socket shape for a specific residual limb of a patient is determined using a computer program. Shape features of interest for achieving a fit to the specific residual limb are then extracted from the desired prosthetic socket shape. An electronic-shape file and socket-shape pair is selected from the database based on the socket-shape in the database that appears to most closely match the desired prosthetic socket shape. Fabrication of a prosthetic socket as defined by the electronic-shape file of the pair that was selected is simulated, using a transfer function that characterizes changes in key features of the prosthetic socket produced using the electronic-shape file of the pair that was selected. The transfer function produces a predicted manufactured shape of the prosthetic socket that might thus be fabricated using said electronic-shape file. Next, the predicted manufactured shape of the prosthetic socket that might thus be fabricated is compared with the shape features of interest that were extracted from the desired prosthetic socket shape for the specific residual limb. The method further determines if any errors that are detected are within predetermined tolerances, and if so, uses the electronic-shape file that was selected to fabricate a prosthetic socket to fit the residual limb. Conversely, if any errors detected are not within the predetermined tolerances, an adjustment is made to a plurality of shape control points in the electronic-shape file that was selected, and the steps of simulating and comparing are repeated, using the electronic-shape file that was selected and modified. If necessary, the steps of adjusting the plurality of shape control points and carrying out the steps of simulating and comparing are iterated using the electronic-shape file as last modified, until results of the step of comparing are within the predetermined tolerances. At that point, the electronic-shape file that was selected and as last modified can be used for fabricating the prosthetic socket to fit the residual limb.

The method then further includes the step of adding a new pair to the database, wherein the new pair comprises the electronic-shape file as last modified, and a shape of the prosthetic socket that was actually fabricated using the electronic-shape file as last modified.

Also, the step of comparing the predicted manufactured shape of the prosthetic socket that might thus be fabricated with shape features of interest that were extracted from the desired prosthetic socket shape can include the step of comparing only specific regions of the predicted manufactured shape and corresponding regions of the shape extracted from the desired prosthetic socket shape. Further, these regions can be weighted according to a likely impact of each region on comfort, or health, or stability, when a fabricated prosthetic socket shape is used on the residual limb, the specific regions comprising the features of interest.

The step of providing an indication of a magnitude and a location where the shape of the prosthetic socket deviates from the shape of the reference can include the step of displaying a map of the differences between the shape of the interior of the prosthetic socket and the shape of the reference and can include the step of indicating at least one of a volume difference between the prosthetic socket and the reference, maximum radii differences for each of a plurality of different regions of the prosthetic socket, regional volume differences for each of a plurality of different regions of the prosthetic socket, regions of consistent error between the shape of the prosthetic socket and the shape of the reference, and distances between feducial points in the shape of the prosthetic socket and corresponding distances between feducial points on the shape of the reference.

Another aspect of the present novel approach is directed to an exemplary system for assessing a prosthetic socket to determine an interior shape of the prosthetic socket and a deviation of the interior shape relative to a shape of a reference. The system includes a digitizer having a stylus ball that is moved relative to and in contact with a surface of the interior of the prosthetic socket. The digitizer has a plurality of encoders for producing signals indicative of a position of the stylus ball in at least two different directions while the surface is being scanned by the digitizer. Also included is a computing device that is coupled to the digitizer to receive the signals from the encoders. The computing device includes a memory in which machine executable instructions are stored, and a processor that is coupled to the memory. The processor executes the machine instructions to implement a plurality of functions that are generally consistent with the steps of the method described above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIGS. 1A-1D (Prior Art), which are borrowed from a website of a company that fabricates prosthetic sockets, respectively illustrate a personal computer display showing a socket shape as designed by a practitioner, a positive model being carved for use in producing the socket, thermoplastic being formed over a positive model to produce a prosthetic socket, and an exemplary socket that has been trimmed and is ready for use by a patient;

Figure 6A:
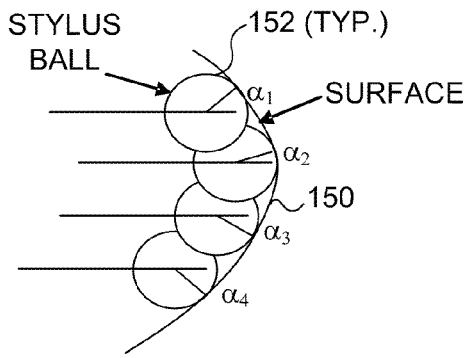
Figure 6B:
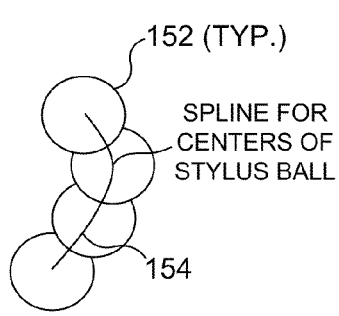
Figure 6C:
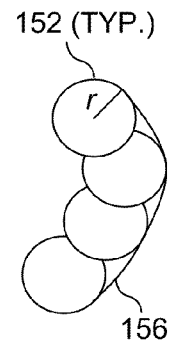
Figure 7:
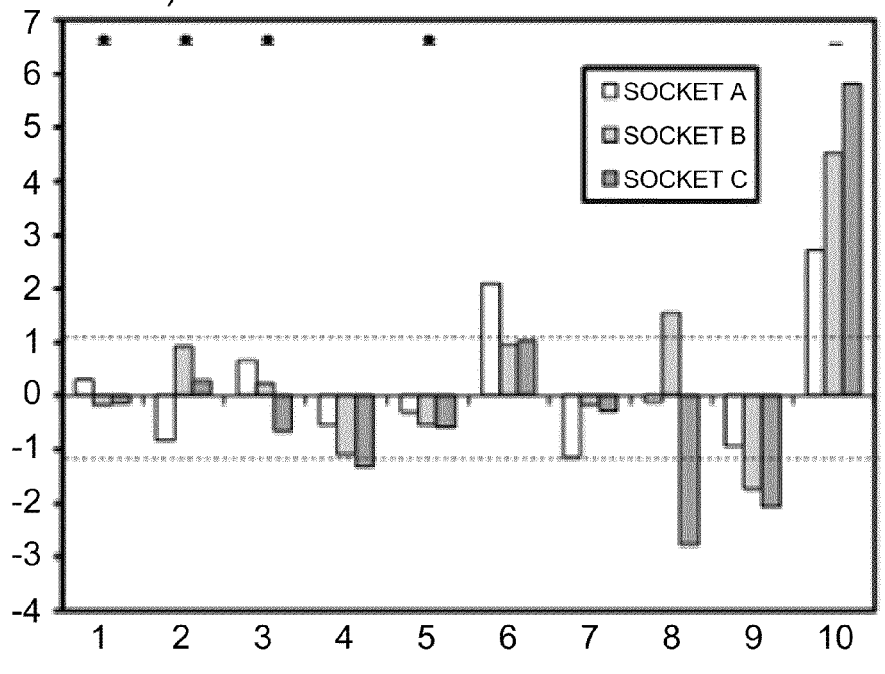
Figure 10:
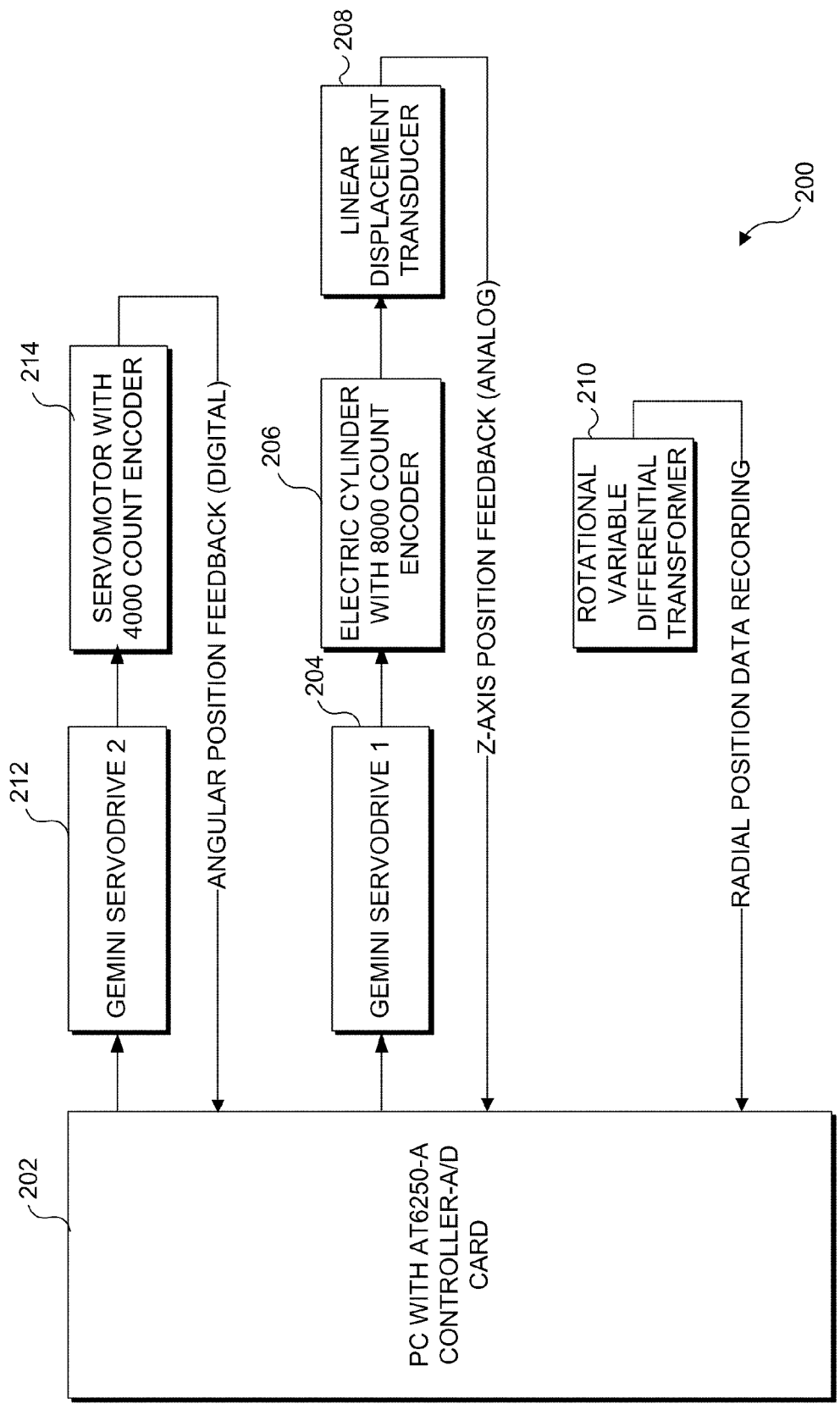
Figure 11:
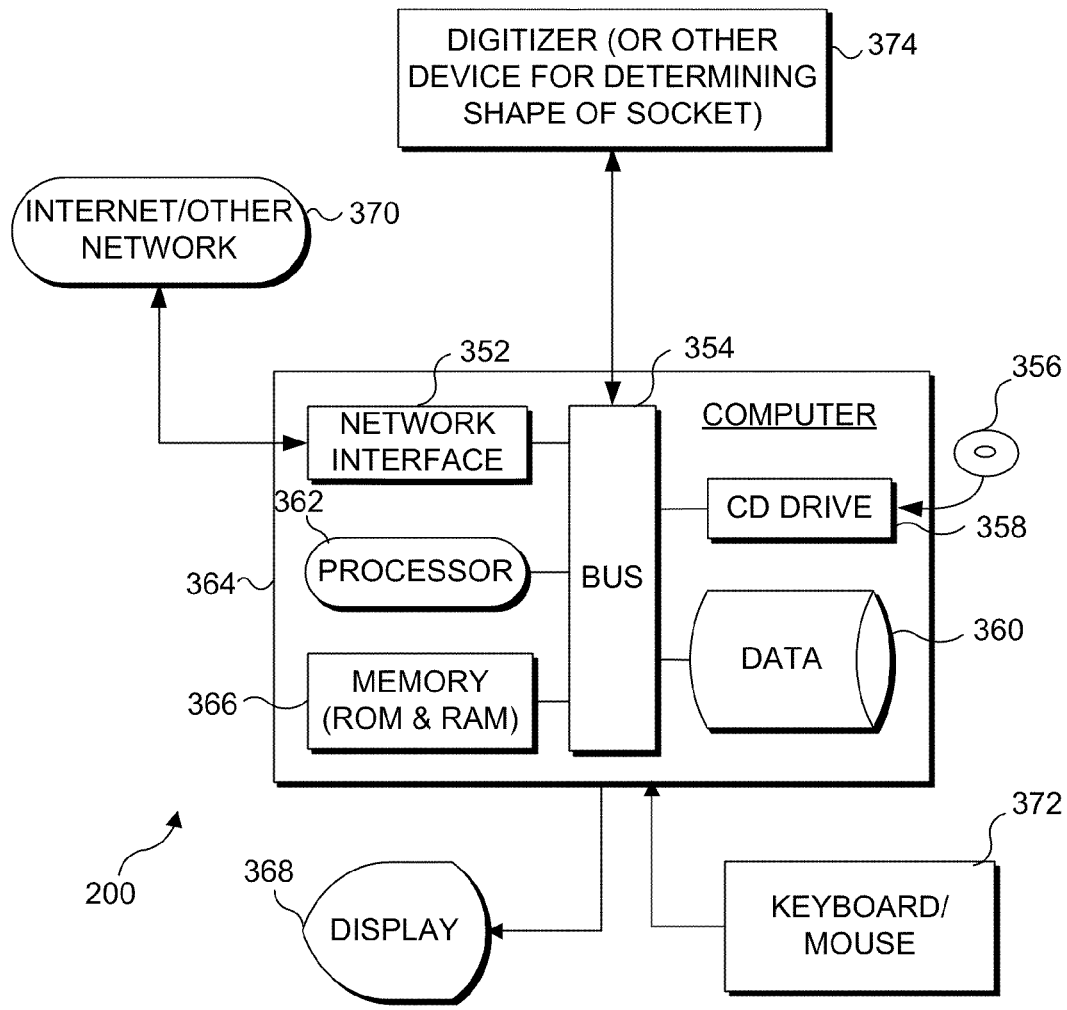
Figure 12:
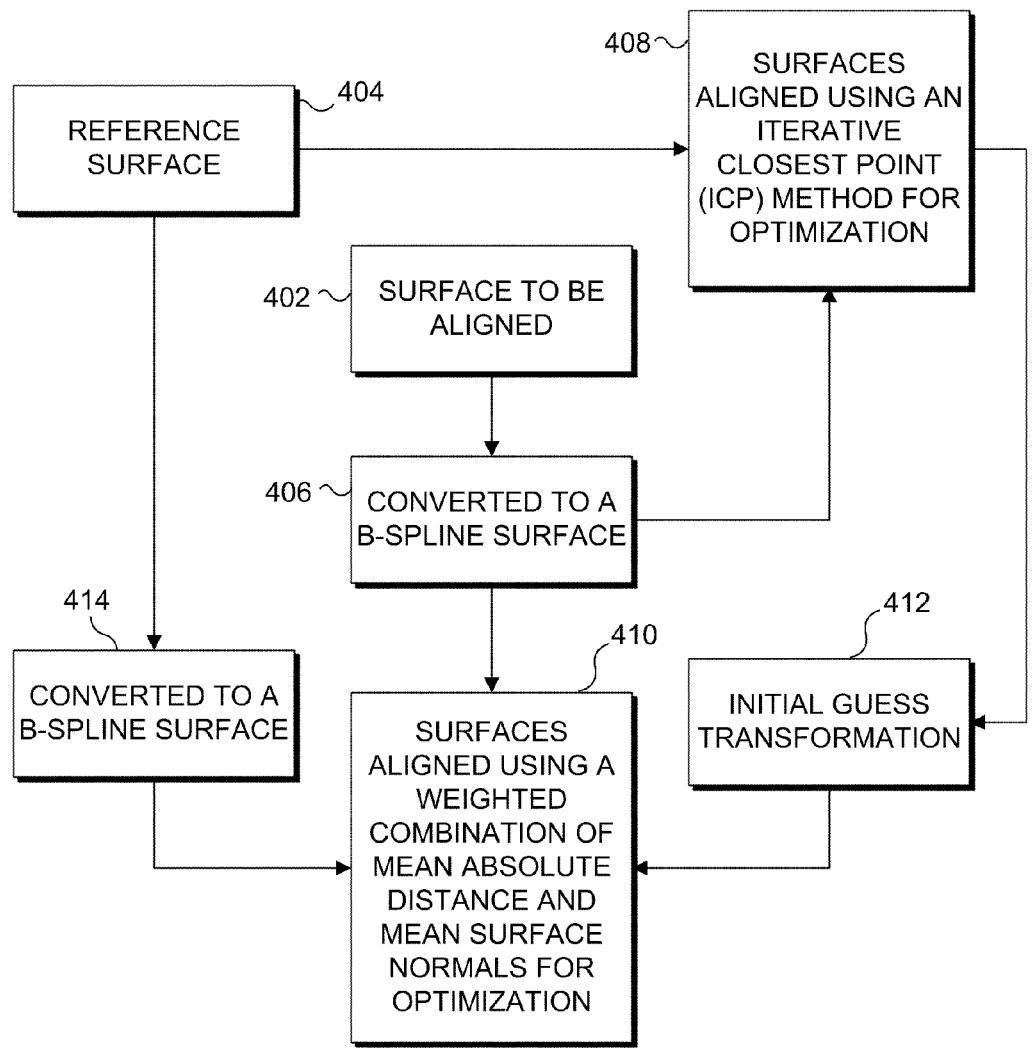

FIGS. 6A-6C respectively schematically illustrate how a contact stylus ball of the digitizer contacts a convex surface in successive slices, the splining of the locations of the center of the stylus ball, and the projection of the spline outwardly in a direction normal to the spline for a distance equal to a radius of the stylus ball;

FIG. 7 is a graph illustrating example volume differences between three sockets fabricated at 10 different fabrication companies and the corresponding electronic shape files that define the desired shapes of the three sockets;

FIG. 8 is a schematic illustration that was published in *Computer Aided Design* 34: 19-26, 2002, which serves as an example to show a retracted surface and an actual surface that is generated by displacing the retracted surface one stylus ball radius outwardly;

FIGS. 9A-9D respectively illustrate socket regions for an anterior view, a posterior view, a lateral view, and a medial view of an exemplary socket;

FIG. 10 is a functional block diagram of an exemplary digitizer and computing device that is usable for scanning sockets and other objects in accord with the present novel approach;

FIG. 11 is a functional block diagram of a generally conventional computing device, such as a personal computer (PC), which is suitable for controlling the digitizer for scanning a socket and other object and for processing the scan data to determine the shape of a socket and other object and for comparing the shape that was scanned to that of an electronic data file, another socket, a residual limb, or a positive model; and FIG. 12 is flowchart illustrating exemplary steps for alignment of a surface of a prosthetic socket to a reference surface.

DESCRIPTION

Figures and Disclosed Embodiments are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Overview

Figure 2:
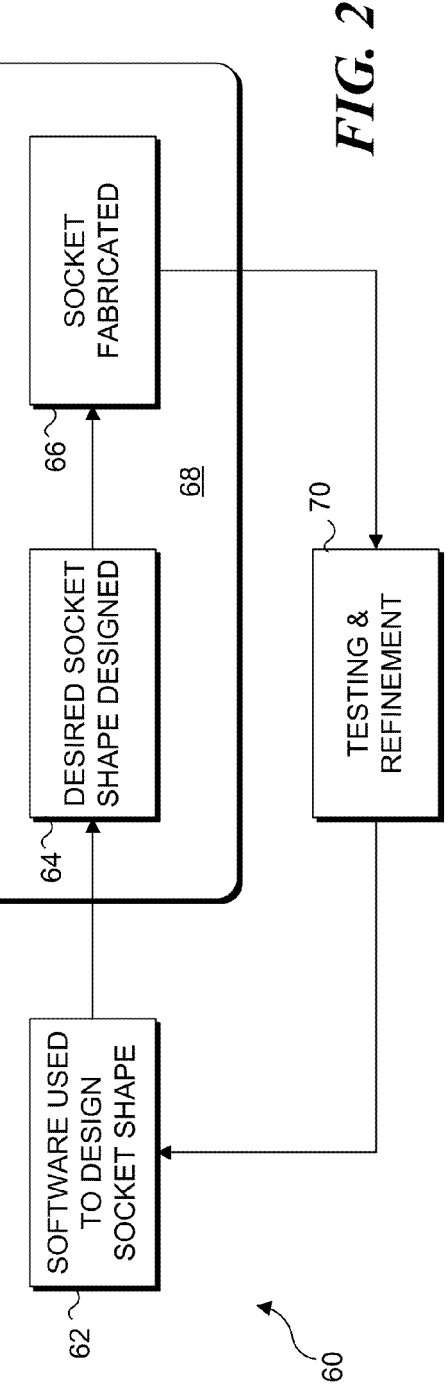
FIG. 2 is a schematic block diagram illustrating how the conventional CAD/CAM procedure for fabricating a socket serves as a focus of the present novel approach, to enable improvements in the process to be achieved.

As indicated in a schematic functional block diagram 60 shown in FIG. 2, the present approach is applied to the generally conventional technique for creating a prosthetic socket using CAD/CAM. As shown therein, in a block 62, a practitioner uses software to design a socket, producing a desired socket shape in a block 64. This desired socket shape is used for controlling the carving process to fabricate a positive model used to form a socket, as indicated in a block 66. The fabricated socket is then provided to the patient, as shown in a block 70, for testing its fit on the patient's residual limb, and for refining the shape of the fabricated socket as necessary to achieve a comfortable fit. A novel approach 68 in accord with the following discussion addresses blocks 64 and 66 in this process, since it enables the fabricated socket to be measured and evaluated by comparison to the electronic file corresponding to the desired socket shape or by comparison to the shape of another socket, or the patient's residual limb, or a positive model—even before a fabricated socket is provided to the patient for testing and refinement or fitting. Further, as discussed below, the present approach can provide a solution to the inverse problem, i.e., of enabling the electronic file that defines the desired socket shape to be modified to correct for errors that have been determined to consistently arise in the fabrication of a socket by a specific fabricator or source, so that the socket actually fabricated and provided to the patient is thereby likely to more closely match the desired socket shape originally created. More details of this process are discussed below.

The present novel approach for assessing the fit of a prosthetic socket comprises both hardware and software components. One exemplary embodiment of the hardware component comprises a very precise shape measurement instrument that uses a contact stylus to measure the shape of a socket interior surface. An earlier design for another embodiment of a hardware component has been previously described in a 2003 publication. However, that earlier embodiment was found to be incapable of the resolution and accuracy required for achieving the desired assessment. In the new exemplary embodiment of the hardware component, there were some crucial refinements that achieved much better results in measuring the shape of the interior surface of a socket. The refinements include: (a) a modification to the stylus so that it can measure areas with very high curvature; (b) changes to the sensors and controller to reduce error and make performance only minimally sensitive to a position of the socket in the measuring device; (c) addition of a gearbox to offset the axis of the hardware component so that the shape of positive molds (i.e., the exterior surface of an object) can also be assessed; and, (d) a modification to the motor controller so that sampling is performed at equal angular intervals. The new approach includes several other differences compared to the earlier approach, as follows: (1) a correction algorithm uses the centers of the stylus ball positions; (2) the stylus ball slides on the surface, instead of rolling; (3) calibration is provided for z-axis displacement from angulation of the arm; and, (4) the surface being scanned is reassembled in r-z rather than r-θ.

Also, in regard to an exemplary embodiment of the software component, there has recently been a refinement of the shape reconstruction algorithm so that splines are assembled in r-z planes, rather than r-θ planes. The algorithm has also been modified so that the shape of a socket is reconstructed in three dimensions (r-θ-z) instead of two, thereby enhancing the accuracy of the socket shape determination process and further reducing a sensitivity to the position of the socket in the device (e.g., errors caused by an axial offset of the socket relative to the axis of the digitizer hardware component). The calibration algorithms have been improved and calibration added to correct for the z-offset from angulation of the stylus arm. Rather than calibrating the instrument output to the position of the surface of the stylus ball in contact with the surface being measured, calibration is now performed relative to the centers of the stylus ball. Then the surface being measured is determined by outward normal projection for a distance that is equal to the stylus ball radius.

It must be emphasized that several other types of instruments can be used to measure the shape of the outer surface of a positive mold (e.g., a laser scanner, a digital camera with a Polhemius sensor, a device using structured light projection, and a contact handheld digitizer). Manufacturers of such instruments include Biosculptor, Medico Supplies Inc., Vorum, Ohio Willow Wood, and Orten. However, compared to measuring the outer shape of a positive model of a residual limb, the task of measuring the shape of an interior surface of a socket is much more difficult because of the limited space available for an instrument that must be inserted into a socket to scan its shape. For a lower limb socket, the diameter of the socket cavity can be less than 10 cm. For such tasks, mechanical digitizers can be employed that have a mechanical arm and which have a contact stylus sized to be inserted within the socket during the measurement process. An exemplary digitizer of this type is described below in greater detail.

The software component that is used for comparing shapes is a key to this new approach. An important feature of the algorithm used in the software component is that it is specifically tuned to prosthetic sockets. An optimization procedure is used to align features of greatest clinical relevance to shape matching. This exemplary algorithm differs from that described in prior publications in several respects. For example, about 180 points per slice from the spline are currently used in the optimization, instead of only a small percentage of the points. Another change is the weighting of the absolute difference between the shape of the scanned surface and the design data, to the difference normals to the surface that is used in the current novel approach. The earlier approach only relied upon the volume difference between the shape of the scanned surface and the design shape data. These changes were found to be important when comparing prosthetic socket interior shapes since the socket shapes have greater definition than many other types of objects and are less likely to comprise gradually varying surfaces than, for example, the outer surfaces of residual limbs.

Tests of commercially available digitizers that have been developed (purportedly) to digitize prosthetic sockets have shown that such devices are unable to measure socket shape with sufficient accuracy to achieve the functionality achieved by the exemplary hardware component described herein. The conventional commercial devices introduce too much distortion in the measurement process to enable an accurate assessment of socket shape.

Software programs have been created to enable the design of prosthetic sockets, and such programs are commercially available. Some of these programs can calculate socket volumes and cross-sectional areas. Examples of such programs to design sockets include OMEGA TRACER™, available from Ohio Willow Wood, Mt. Sterling, Ohio; BIOSHAPE™, available from Biosculptor, Hialeah, Fla.; and SHAPE-MAKER™, available from Scheck and Siress, Chicago, Ill. While none of these software programs are able to compare two scanned shapes or to compare a scanned shape with an electronic shape file, it appears that it may be possible to modify these commercial software packages to include the shape comparison algorithms comprising the software component of the present novel approach.

Figure 1A:
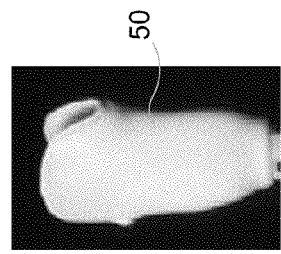
Figure 1B:
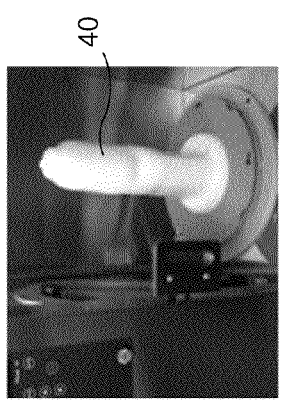
Figure 1C:
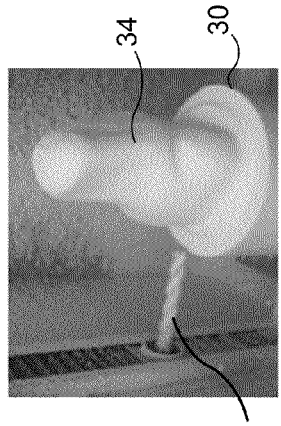
Figure 1D:
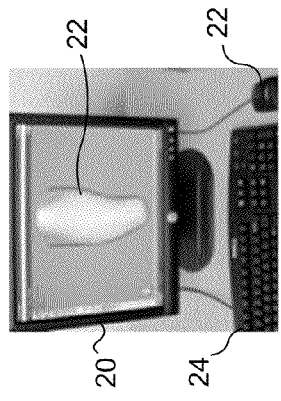

Two assessments have been made using this novel approach. In the first assessment, the shapes of carved positive models (like those shown in FIG. 1B) were compared with the electronic shape files that were input to the carvers to produce the positive models. Results showed that errors occurring during carving were, in general, less than those occurring during forming of a socket. This finding seems logical, since during forming, shrinkage of the polymer used to make the socket likely contributes to much of the shape distortion, since the shrinkage of commonly used thermoformable polymers has been measured up to 18%. Further, the errors that were noted tended to be more uniform over the surface for the carved positive models than for the sockets. The conclusion is that the most significant source of problems with CAD/CAM produced sockets occurs during the forming process.

In the second assessment, the relationship between the shape analysis results and a clinical evaluation of socket fit were evaluated. Results showed that in general, the shape difference determined using the present novel approach maps well and matches the areas of poor socket fit in need of modification. A surprising result was how many computer-manufactured sockets were immediately rejected using the present novel method for measuring shape and comparing the measured shape to the desired shape, because of volume mismatch problems.

Details of An Exemplary Scanning and Digitizing Component

Figure 3:
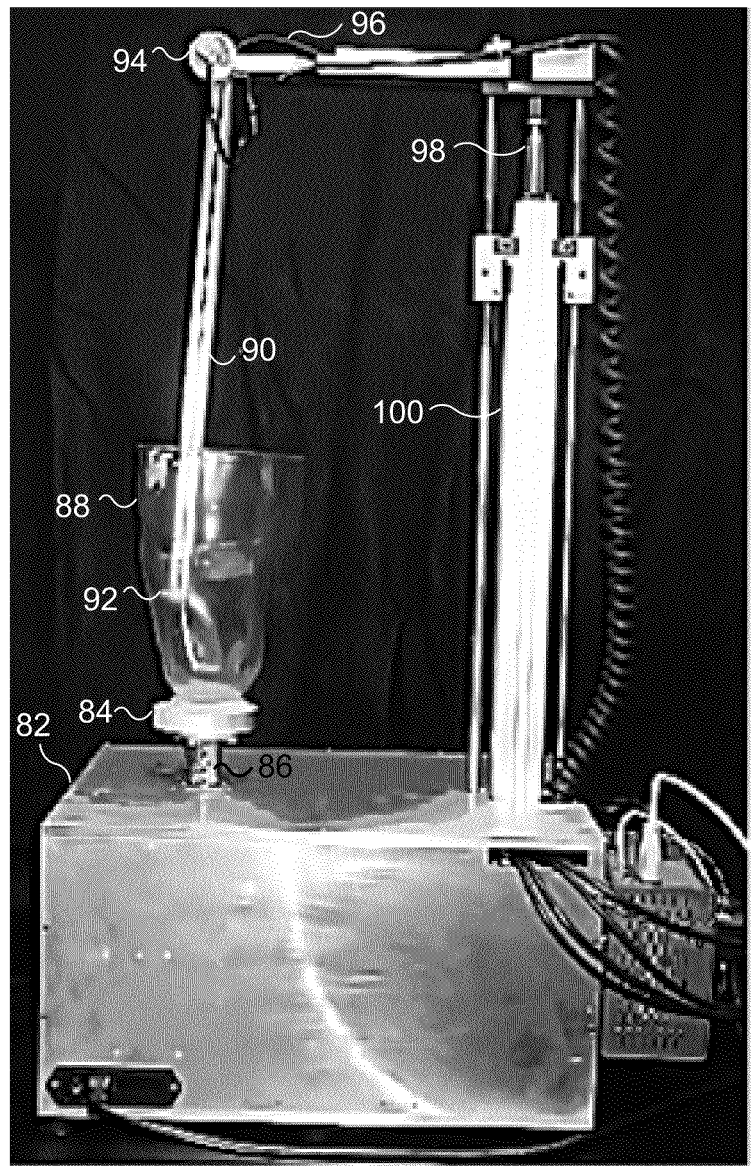
FIG. 3 is an exemplary embodiment of a custom shape measurement digitizer component used in the novel system described below for scanning the surface of a prosthetic socket or other object.

FIG. 3 illustrates an exemplary digitizer 80 that includes a servomotor (e.g., a Compumotor model SM232™, Rohnert Park, Calif.) housed in a base 82, a servo-electromechanical cylinder 100 with a linear rod guide 98 (e.g., a Parker-Daedal model ETB32™, Irwin, Pa.), a servo-controller (AT-6250™, available from Compumotor), which is not shown in this Figure, a rotational variable differential transducer (RVDT) 94 (e.g., a Schaevitz model R30A™ with ATA2001™ amplifier (not shown), Hampton, Va.), a linear displacement transducer (LDT) (BTL-5-A/C/E/G1-M457-R-S32™, available from Balluff, Florence, Ky.), which is not shown in this Figure, a four-bar linkage 90, a spring steel 96, and a stylus 92. The digitizer uses a full contact method in which a stylus is always in contact with the object being scanned and digitized. The radial, angular, and vertical positions of the stylus with respect to a socket 88 are recorded as the socket is rotated around the stylus on a turntable 84. The turntable is driven by an electric motor (not shown) disposed in base 82, by a shaft 86, producing data that are stored in a non-volatile memory, such as on the hard drive of a personal computer (not shown in this Figure). It is also noted that an optional additional gearbox (not shown) can be provided in the base, to offset the index table relative to the stylus and ball, so that an exterior shape of an object other than a socket, such as a positive model of a residual limb or a positive model of a desired prosthetic shape, can be scanned and digitized.

In this exemplary digitizer, the socket is connected to the servomotor via a split coupling that has different mounting capabilities (e.g., including a straight post, or a mounting platform for assembled prostheses). The servomotor uses an encoder (with an angular precision of 0.045°) for position feedback control and angular position data. The vertical position is controlled with a positional feedback servo-electromechanical cylinder. Vertical position data are recorded with the LDT, which is mounted between the base of the electromechanical cylinder and the cylinder piston.

Attached to the top of the piston is the RVDT and a four bar linkage-mounting arm. This mounting arm provides a fixed position for the linkage and is designed so that the center of rotation of the stylus is directly over the center of the servomotor shaft. Thus, the mounting arm acts as a ground arm for the four-bar linkage. Two rods of the linkage are attached via Vee-Jewel pivots, with the pivot on the front rod connecting directly to the RVDT and providing an angular measurement for the rod. The angular measurement is converted into a radial displacement of the stylus. The stylus is the fourth link of the four-bar linkage and also connects to the rods with Vee-Jewel pivots. The entire system is designed so that the stylus remains horizontal, despite the angular rotation of the linkage. The contact point of the stylus is a 3.175 mm diameter sapphire ball (sphericity 0.000635 mm), the smallest size available commercially for which a stable holder could be accurately machined. The Vee-Jewel pivots and sapphire balls were selected for use in this exemplary digitizer based on their characteristic resistance to wear and low coefficient of friction (0.05 on steel, 0.01 on sapphire). A 0.54 mm thick elastomeric bias member (i.e., spring steel 96) is mounted at the top of the four-bar linkage to ensure a consistent force is applied from the stylus to the socket.

For prosthetic casts or residual limb molds to be digitized, a different setup is used. A precision gear head (not shown) is mounted on the servomotor to offset its axis of rotation. The major components of the gear head are its input and output shafts, drive gear, driven gear, and precision bearings. The gear head input shaft (which is pressed into the drive gear) connects directly to the servomotor shaft via a split coupling. The output shaft (which is pressed into the driven gear) has the same mounting capabilities as the system without the gear head. The gear head is designed with a 1:1 ratio, so that no precision is lost as a result of the angular position. The total offset of the rotational shaft is 8.89 cm. Because the gears are rotated in only one direction, backlash is not a problem.

Voltage signals from the RVDT and the LDT encoders are input to a PC (personal computer) that controls and records data from the digitizer through a 14-bit analog-to-digital (A/D) board (OPT-AT6250-A™, available from Compumotor) and recorded with the use of a custom algorithm (Labview™, available from National Instruments, Austin, Tex.). Angular output signals are recorded directly with the AT6250™ controller. The theoretical precision of the RVDT is 0.00968°/bit. With a four-bar arm length of 441.5 mm, the digitizer thus has a radial precision of 0.07459 mm/bit. The LDT has a theoretical precision over the entire vertical range of 0.05579 mm/bit. Further details of the scanning system are described below in connection with FIGS. 10 and 11.

Calibration And Evaluation of the Digitizer

To calibrate the digitizer, axisymmetric test objects with precisely machined radii were used. Stepped cylinders and stepped vessels were employed, having sections with radii of 25 mm, 35 mm, 45 mm, 55 mm, 65 mm, and 75 mm. A 250 mm long cylinder was also used, and it had a constant radius 50 mm. Calibration equations were developed to convert the three digitizer outputs—servomotor position, electromechanical cylinder position, and RVDT position—to spatial cylindrical coordinates of the center of the stylus ball. Information from the motor encoder, RVDT, and LDT was used to establish the alignment of the motor axis relative to the slide rail axis, and to calculate linear relationships between the RVDT voltage output and the angle of the stylus arm. The LDT output was correlated to height using a precision vertical height sensor (HDS™, Mitutoyo USA, Aurora, Ill.) as a standard. The factory calibrations of the servomotor and electromechanical cylinder were verified as being within tolerance and were thus used as supplied. The results of the calibration confirmed the factory calibration of the RVDT, and the fabrication and assembly of the digitizer were found to be well within tolerance. No systematic trends were observed in the residual error, which had a mean of zero and standard deviation of 0.05 mm.

To evaluate the performance of the digitizer, a test object was scanned in different orientations. More specifically, a right circular cylinder with unknown surface roughness and eccentricity was positioned in the digitizer so that it was visually well aligned with the servomotor axis. Three scans were performed, and the object was then removed, flipped 180°, and rescanned three times. It was then translated approximately 1.5 cm and rescanned twice. Next, it was tilted approximately 20° and rescanned twice. For each of the 10 scans, the radius of the cylinder was computed from the reconstructed object. Consistency in the shape measurement among the scans was assessed. The mean radius was 46.75 mm (standard deviation of 0.076 mm). The radius of the cylinder as measured by a digital vernier caliper was also 46.75 mm. The root-mean-square (RMS) error was 0.075 mm in the radial direction, 0.05° in the tangential direction, and 0.1 mm in the vertical direction. The time for digitization was 90 s/slice for the resolution settings just described.

As shown in FIGS. 6A-6C, calibration data are used with measured socket data to reconstruct a three-dimensional (3-D) shape of an interior socket surface 150. The technique employed for shape reconstruction is relevant in understanding a benefit of the novel approach, as described in detail below. Data at the same angular position from adjacent slices, i.e., in the same r-z plane, are fit using Cartesian B-splines. Because the angle ($α_n$) at which a stylus ball 152 contacts surface 150 is not known (see FIG. 6A), the procedure first determines a spline 154 for the locations of the centers of the stylus ball (see FIG. 6B) at each measurement point. Spline 154 is then projected outwardly, normal to the spline, for a distance equal to the stylus ball radius, r, (see FIG. 6C) to produce a new spline 156. This new spline lies on the object surface. From this series of B-splines formed for each layer of measurement, a second set of splines is generated for the orthogonal direction to create a three-dimensional surface.

Evaluations were conducted to assess dependence on socket mounting in the shape measurement device. Small intentional angular (2.5°) and translational (0.5 cm) misalignments of the socket axis in the anterior, posterior, medial, and lateral directions induced minimal error. Volume errors averaged 0.03%, and mean radial error was 0.04 mm. Therefore, as long as the socket shapes being tested were fairly axisymmetric (moderate range of radii values), socket shape was accurately measured. However, error increased substantially when larger misalignments occurred. Because the sockets that will be assessed are not necessarily highly axisymmetric, it was evident that the instrument processing code had to be improved to be less sensitive to this error.

It was determined that the alignment error stems from a reconstruction issue. In this initial approach, the digitizer was calibrated relative to the position of the outer surface of the stylus ball against the cylindrical calibration object. However, this method does not account for the off-axis contact (digitizer radial axis) of the stylus ball with the interior surface. A new approach reconstructs the surface by first creating B-splines from the measured data of the stylus ball centers in r-z planes, and then projecting those splines a distance of one stylus ball radius outwardly, normal to the spline, still in the same r-z planes (FIGS. 6A-6C illustrate this earlier approach). However, this method does not account for off radial-axis contact of the stylus ball in the orthogonal direction (r-θ), resulting in an error. This error worsens in high curvature regions of a socket that is being scanned. Correction for this error can be accomplished as discussed below. It should be noted that this source of error plagues commercial shape-sensing products as well. The technique used in the present novel approach to avoid this source of error is thus generally applicable to the scanning devices used by others in the industry as well.

Because stylus-socket contact in r-z and r-θ planes is not necessarily along the radial axis through the stylus ball center, an unacceptable measurement error results for highly non-axisymmetric socket shapes that are being scanned. A new approach is employed to correct for this error by creating a 3-D surface from measurements of the center of the stylus ball, and projecting normals outward from those locations, using the technique described herein. The normals are projected outwardly in three dimensions, from the retracted surface by a distance equal to the stylus ball radius to achieve the actual surface (see FIG. 8). This technique eliminates error from the stylus contact angle in the r-z and r-θ planes, and the projected points now represent the true 3-D surface of a socket that has been scanned with the digitizer.

To create this algorithm, a tensor product B-spline surface is used as the mathematical representation of the actual surface as well as the measured point set (the retracted surface shown in FIG. 8). Cubic basis functions are used along both the radial and the longitudinal directions since they represent a good compromise between smoothness on one hand, and numerical efficiency and robustness on the other. Lower order representations do not provide sufficiently fine control over continuity to faithfully model some high curvature regions of the socket, while higher order polynomials have larger support regions resulting in denser and more computationally expensive Jacobian matrices in the optimization procedures. Along the radial direction, the first and last three control points are wrapped to model the closed contours, resulting in what are known as periodic B-splines.

The proposed reconstruction procedure of the socket surface includes three steps:
1. Construct a B-spline surface representing the retracted surface like that shown in FIG. 8. The problem of fitting a tensor product B-spline surface to the measured stylus ball centers can be formulated as a linear numerical optimization problem. The parameters of the problem are the locations of the control points defining the B-spline surface. The objective is to minimize the sum-of-squares Euclidian distance between the measured points and the surface. Since the solution requires solving a system of linear equations, the computations involved can be done fairly efficiently.
2. Offset the measured points outwardly along 3-D surface normals of the retracted surface. The positions of the contact points on the socket may be generated by offsetting the measured stylus ball center locations along the normal directions of the retracted surface computed above. Analytical expressions for the normal direction vectors are readily available from the B-spline representation and can be used to compute offset coordinates.
3. Construct a B-spline surface to fit the offset points. This B-spline surface is used as an initial guess of the spline describing the interior surface of the socket.
4. Optimize the shape of the initial guess B-spline surface. This problem can be formulated as a nonlinear numerical optimization problem to compute control point locations so as to minimize a Euclidian sum-of-squares distance between the stylus ball centers and the B-spline surface. (Note that the projection from the stylus ball centers to the inner socket surface serves as an initial guess. An optimization is then carried out in the opposite direction, from the new surface to the stylus ball centers, adjusting the control points on the new surface (i.e., the inner socket surface B-spline) to achieve the optimization. This step is implemented because the surface that is to be accurately determined is the inner socket surface, not the splined surface through the center of the stylus ball points.) Even though the stylus ball centers do not lie in parallel planes along the vertical axis of the socket, the objective function and its derivatives can be computed efficiently because of the underlying parameterization of the point set. Jacobian and Hessian matrices, which are involved in the optimization, are also fairly sparse, and problems with a few thousand control points can be performed routinely on modern desktop computing machines in very little time. Further, a good initial guess for the optimization process is the solution of the linear least squares problem of fitting the B-spline surfaces to the offset points computed in step 3. Other offset surface approximation procedures can alternatively be employed.

In addition to this enhancement in the data processing algorithm to correct for off-axis stylus ball contact angle in three dimensions, the present novel approach corrects for the z-axis offset from angular displacement of the stylus arm, which is done on a point by point basis. This calibration is incorporated into the data processing algorithm to avoid excessive error. The calibration is done using the known geometry of the stylus arm and the stylus arm radial position, which is determined from the RVDT signal. Another change from the earlier approach is the sampling at equal angular intervals, rather than at equal time intervals, as described above, and as noted in FIG. 10. No other modifications to the earlier design of the shape-measurement instrument are necessary. The digitizing device meets the needs for accurately scanning the interior surface of prosthetic sockets. Weekly testing and daily calibration using test objects of known shape can be conducted to ensure consistent performance of the digitizing system over time.

Shape Comparisons

Custom algorithms that were developed are used in the present approach to compare data defining the shape of a prosthetic socket to a reference. The reference is provided as data defining a residual limb shape, an electronic data file created to define the desired shape of a socket, data defining a shape of a positive model of a residual limb, data defining a shape of a positive model of an intended socket shape, or data defining the shape of another socket. The shape alignment algorithm is an optimization procedure that uses a weighted linear combination of maximized global similarity and maximized local shape similarity. First, an iterative closest point method, i.e., the minimization of the sum of the squared distances between all points on the first shape and the closest points on the target shape, is used to establish an initial guess of the alignment optimization. To maximize global similarity, the minimum weight-matching variant of the bottleneck-matching method is used, minimizing the sum of the absolute distances (i.e., mean radial error) between corresponding radii on the two point-sets, which is an approximation of the volume of symmetric difference. To maximize local shape similarity, the difference in angle between corresponding surface normals is minimized, using the negative mean hyperbolic arc tangent of the dot product of corresponding surface normals. This algorithm has proven extremely robust in prosthetics applications and has been used to effectively characterize residual limb shape changes measured over time, shape differences between sockets and electronic shape files, and shape differences between positive models and shape files. It represents an advancement over previous shape alignment efforts that exclusively used a minimization of volume difference, anatomical landmarks, or top and bottom slice centroids.

Testing of the algorithm on limb shapes with localized modifications showed exceptional performance. For three residual-limb shape-change conditions tested and compared with a reference, root-mean-square errors were 0.004 mm in translation and 0.012 degrees in rotation. These errors result in minimal change for the calculated features of interest.

Evaluation of Sockets and Carved Positives Made by Central Fabrication Facilities The shape measurement instrument and algorithms described above were used to assess trans-tibial sockets and carved positives made by central fabrication facilities. Analysis of carved positives has been done using the digitizer and approach described above, with the exception that the model surface has previously been determined by projecting surface normals to positions of the stylus ball inward, instead of outward as is done in the present novel approach. When the instrument is used to assess models, the projection is done in the other direction, i.e., using inwardly directed normals.

Thus, it is possible to compare errors resulting from the carving stage to those resulting from the forming stage for each different fabrication facility being evaluated.

Central fabrication facilities are companies that receive desired socket shapes from customers as transferred electronic data files, fabricate the carved positives and form the sockets using CAM methods, and then send the sockets (and/or carves if requested) back to the customers. There are standard formats for these electronic data files used in the prosthesis industry, and these may evolve over time to meet changing needs.

Ten central fabrication facilities located within the continental U.S. were each contracted to make three carved positive shapes and three sockets. The chosen three subject cases were selected because they represent a range of shapes encountered clinically—tapered; bulbous; and, cylindrical with bony prominences. The electronic data files specifying these shapes were sent to the central fabrication facilities electronically via e-mail.

Socket and carved positive shapes were measured with the custom shape measurement digitizing device described above. The instrument was calibrated each morning before use. All sockets and carved positives were assessed at a density of 800 points per slice, at a slice spacing of 0.8 mm to 1.75 mm. A slice spacing in the lower end of the range was used when curvature changes dictated that it was necessary. Measured shapes were compared with the electronic data shape files sent to the central fabrication facilities using the alignment algorithm described herein.

Results of the evaluation showed that 20 of the 30 sockets in the study had volumes within a range of −1.1% to +1.1% of the volume specified by the corresponding electronic data shape file, as shown in a graph 160 in FIG. 7. A 1.1% volume difference corresponds approximately to 1 sock ply (~0.25 mm thickness), using Fernie's limb model. Thus, clinically, a patient would need to add or remove sock(s) to use a socket with an absolute volume difference of 1.1% or greater. Four of the companies (Nos. 1, 2, 3, 5) made all three sockets within the −1.1% to +1.1% volume range, and one company (No. 10) made all three sockets outside this range. The other five companies made one or two sockets within the range. Thus, there was a wide range in consistency among the companies evaluated. Also, while not true for all of the companies, it is apparent that for many of the companies (Nos. 4-7, and 9-10), the errors were consistent in regard to all of the three sockets fabricated by the company. This observation is important because it suggests that the nature of the error by a specific company in fabricating a properly fitting socket might be used to determine how to correct such errors in the fabrication process by modifying the electronic data shape file before it is used in the fabrication process, so that the resulting socket has minimal error and closely matches the desired design socket shape. This technique is discussed below in regard to the "inverse problem."

Inverse Problem

In a related study, it was determined that a number of different anatomical regions of the residual limb might be used for evaluating the fit of sockets produced by different fabricating companies. Then, by measuring the errors in the fit of a characteristic sampling of the sockets produced by a specific fabricating company for those regions, it might be possible to determine corrections that can be applied to the desired design electronic data file before a socket is fabricated by the company, to ensure that the resulting socket actually closely matches the original desired design shape for the socket. For example, the corrections can be related to errors determined for a specific fabricator in each of 17 different anatomical regions of the residual limb. The regions selected are merely exemplary and are not intended to limit the scope of this concept, since it is likely that further refinement will lead to a choice of either fewer or more or even different anatomical regions for characterizing consistent errors.

Figure 9:
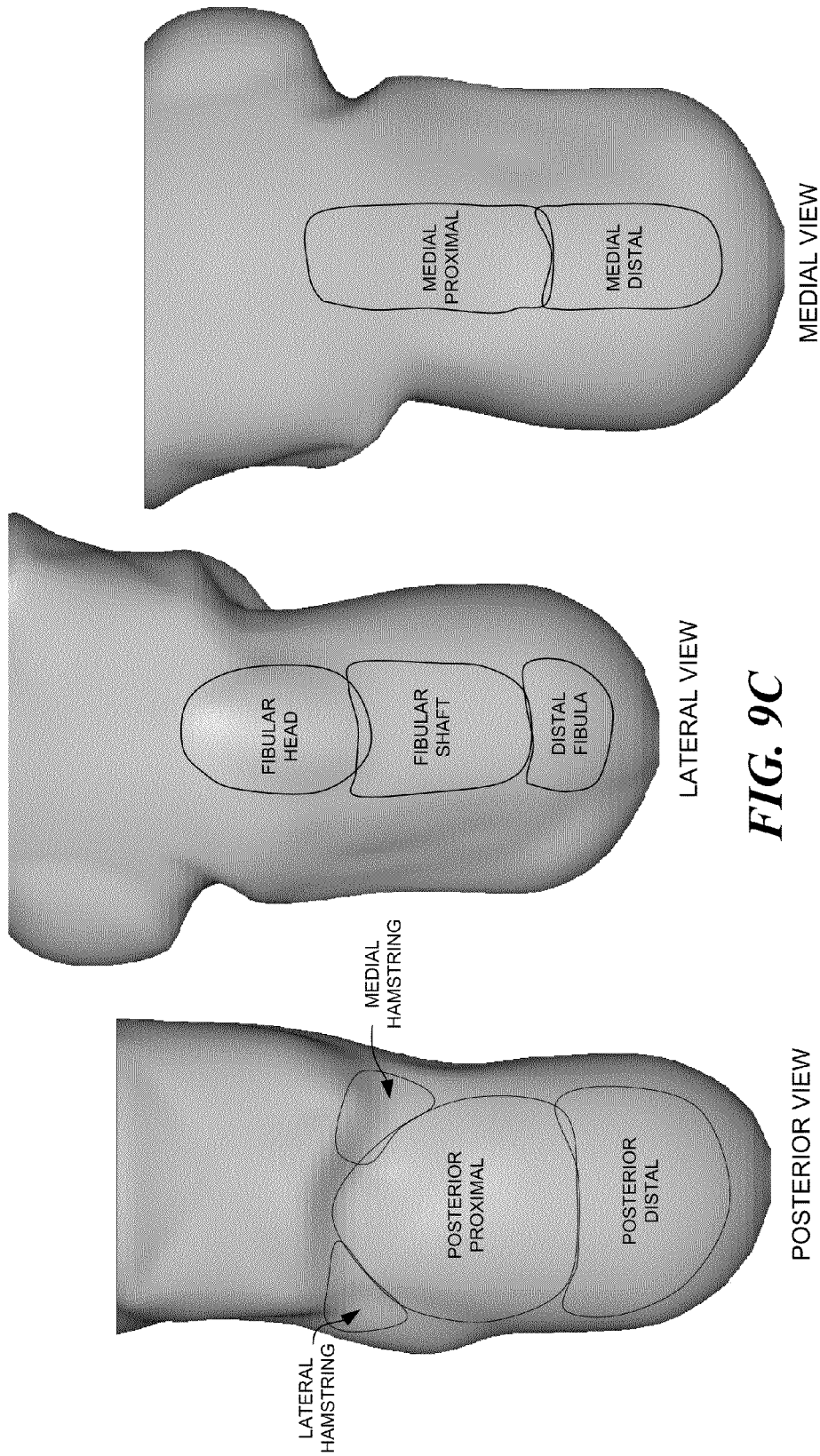

The regions are computationally defined based on anatomical landmarks (e.g., mid-patellar tendon, tibial crest, tibial end) and socket contour analysis, similar to "socket template" definition procedures used in commercial prosthetic design software packages (e.g., ShapeMaker™ by Scheck and Siress, Naperville, Ill., Biosculptor™ Shape Manipulation Software by Biosculptor, Hialeah, Fla., and Tracercad™ software by Ohio Willow Wood, Mt. Sterling, Ohio). The anatomical regions are allowed to overlap, and region characterization can be standardized across subjects. As illustrated in FIGS. 9A-9D, the seventeen exemplary regions are clustered by views, as follows:

FIG. 9A—Anterior View: patellar tendon, medial condyle, lateral condyle, tibial tuberosity, medial flare, lateral flare, anterior tibial crest, and anterior distal tibial;

FIG. 9B—Posterior View: lateral hamstring, medial hamstring, posterior proximal, and posterior distal;

FIG. 9C—Lateral View: fibular head, fibular shaft, and distal fibula;

FIG. 9D—Medial View: medial proximal, and medial distal.

Again, it must be emphasized that these anatomical regions are intended to be exemplary and not in any way limiting on the approach disclosed herein; they were developed based on clinical fitting experience, as well as early experience using the present novel approach. As model development proceeds, it is likely that they will be adjusted as deemed necessary to achieve optimal results.

Figure 5:
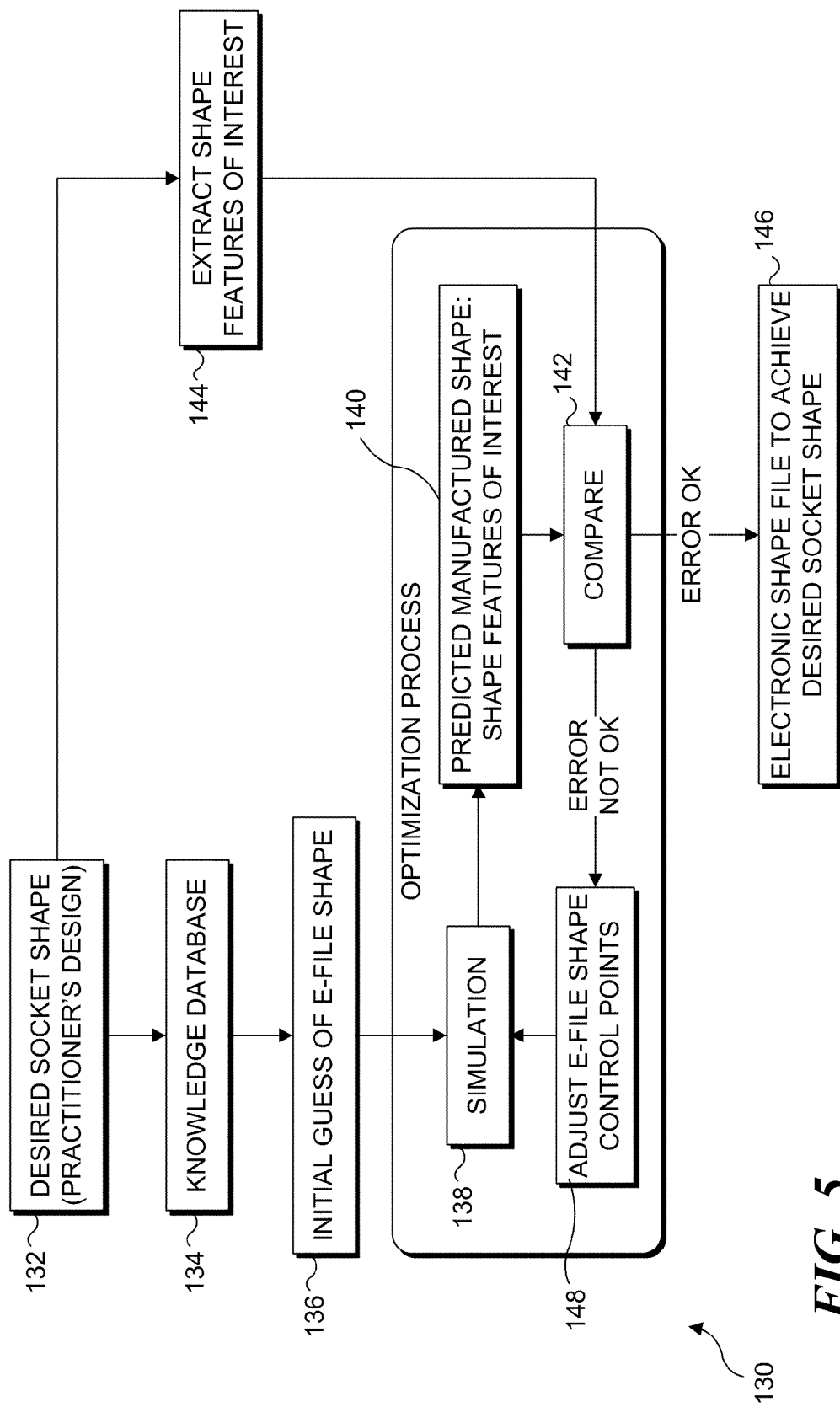
FIG. 5 is a flowchart illustrating exemplary logical steps for solving an inverse problem to determine a more accurate electronic design shape file for use in fabricating a socket, based on a knowledge database compiled for sockets made by a specific fabrication source.

FIG. 5 includes a flowchart 130 that illustrates exemplary logical steps used for employing the present novel approach to achieve a solution to the inverse problem, i.e., it shows the steps used to determine corrections that can be applied before a socket is fabricated so that the socket that is actually produced and provided for fitting to a patient achieves an acceptable match with the desired socket shape that was originally designed. The procedure begins with a step 132, in which a desired socket shape is created that represents the practitioner's design for a specific patient residual limb. This desired socket shape is defined in an electronic data file format and can be efficiently created using a CAD program, as noted above. A step 134 provides for input of the desired socket shape to a knowledge database, which is a collection of electronic-shape-file/actual-socket-shape pairs that were established based on experimental measurements and evaluation of a plurality of sockets produced by a specific socket manufacturing system or source (i.e., a carver and forming method) that is being used to produce the current prosthetic socket. The desired socket shape is compared with the actual socket shapes within this database to select a best match. It may be necessary to linearly scale the actual socket shapes in this comparison so that both volume and shape match well with the desired socket shape. Once the best match actual socket shape is identified, its corresponding paired electronic shape data file is used in a step 136, as an initial guess of the appropriate electronic data file to be input to the optimization process.

In a step 138, the fabrication process is simulated. A simulation engine used in this step implements a transfer function that characterizes the changes in key features of the input electronic file shape when it goes through the manufacturing process at the specific fabricator facility. It seems inappropriate to analyze every point on the socket shape in this simulation because that process is computationally too intensive and, further, does not weight more important anatomical regions heavier than regions of lesser importance. It is the important anatomical regions of a socket shape (characterized in the exemplary list below) that must most closely match the same regions in the desired socket shape. The simulation engine is a general algorithm, although it is expected that the constants used for the actual manufacturing suite being used will be tuned to achieve better results, as experience dictates. Tuning is done using the same data used to develop the knowledge database described above in step 134, although once tuned for a particular product, the tuning should not need to be changed unless that system is modified. It is contemplated that initially, approximately five measured socket shapes/electronic file shape pairs may be necessary to conduct this tuning.

The simulation is developed using one of the following modeling approaches: parametric analysis; finite element analysis; fuzzy logic; neural networks; or some other artificial intelligence approach. The results of the simulation provide the predicted manufactured shape in a step 140, defined in terms of the shape features of interest related to the anatomical regions. The features assessed in this simulation are those clinically relevant to establishing a correct socket shape; weighting can be applied to various features based upon their relative importance in achieving a good fit for a socket. For example, the shape features of interest may include:

1. Distances Between Landmark Points: The landmark points may include the midpoint of the patellar tendon bar; apex of the fibular head; apex of the curve at the anterior distal end; and mid-point of the popliteal fossa. It should be noted that many other landmarks are often used in commercial socket design that could alternatively be used in the present approach. For example, other lower limb landmarks include: tibial crest, interosseous groove (this landmark is in the foot and is thus useful for Syme's or partial foot amputees), level of shelf, popliteal compression, tibial tubericle, tibial tuberosity, (the following are all for trans-femoral amputees) femoral end, femoral shaft, ischium, knee center, trochanter, condyles, and hamstring. Also, if used for above-the-knee sockets, anatomical landmarks on the thigh might be included.
2. Sectional Volumes: The socket shape is segmented into parallel slices perpendicular to the socket long axis. The slice thickness might be smaller in highly sensitive regions (e.g., between the patellar tendon and tibial tubercle) compared with less sensitive regions. It is likely that approximately eight sections will be employed, as appropriate.
3. Regional Shapes: Four regions on the socket must well match the designed socket shape: patellar tendon, fibular head, anterior distal end, and popliteal fossa. Each region is characterized by a surface area, maximum radius, and volume. Other possible regions include: tibial plateau, anterior tibial crest, tibial tuberosity, fibular shaft, distal end of fibula, and brim.

A step 142 then compares the shape features of interest for the predicted manufactured shape from the simulation and the shape features of interest that were extracted in a step 144, from the original desired socket shape created by the practitioner in step 132. The first goal is to characterize the error determined by this comparison. If the error is acceptable (i.e., below a threshold that was established based on clinical experience) then the process is done, and the electronic shape data file selected in step 136 can be used for actually manufacturing the socket, as indicated in a step 146. However, if the error is unacceptable (i.e., outside the threshold), the process determines the control points that need adjustment in a step 148. (The control points are the points that characterize the predicted manufactured shape; a tensor product B-spline is currently used). This step also determines the direction to move the control points so as to reduce the error. It is expected that local shape modifications (i.e., the regional shapes in the list above) will require only local modification of control point locations. Because of a B-spline property known as "local control," wherein a control point only affects the nearest four segments for a cubic B-spline, specific regions can be selected and modified to change an effect they have on the predicted socket shape, while other areas are ignored so that their shape is left unchanged. The sectional volumes will likely require modification to control points within each section. The distances between landmark points will likely require a more global resizing. A new (i.e., modified) electronic shape data file will thus be created based on these adjustments. That data file is then run through the simulation procedure in step 138, and the optimization process is repeated until the error resulting is acceptably low, leading to step 146.

The preceding procedure for determining an appropriate electronic shape data file to be used before a socket is fabricated by a specific fabricating company (so as to correct errors introduced during the fabrication process by that fabricating company) thus avoids the delay resulting from the company producing an improperly fitting socket that must be either remade or modified to properly fit a patient's residual limb (or which may require an excessive number of socks be worn to achieve a less than perfect fit for the patient).

It is contemplated that the solution to this inverse problem might be further simplified if the sockets are represented with a recently introduced method of representing surfaces called T-splines. With T-splines, it should be possible to represent surfaces as accurately as a tensor product B-spline but with about ⅓ the number of control points.

Computational Component

Benefits of Current Novel Approach Relative to Earlier Approach

An earlier approach for processing the digitizer or scanned data was limited in functionality and in the value of the results it produced because it only employed two-dimensional processing to measure the shape of a socket. In contrast, the present approach processes the scan data in three-dimensions, as explained above. In addition, the present approach employs both mean absolute differences and weighted surface normals for alignment. In the earlier approach, and other prior art techniques, only the volume differences were used when comparing the scanned data to the design shape, which does not work well for some shapes. For example, the weighting can be 0.8:0.2 for absolute difference:surface normals when analyzing sockets. In addition, 100% of the points produced by creating a computational surface of a scanned socket are used for a comparison of the scanned data to: (a) the scan data for another socket; (b) an electronic data file defining a socket; (c) scan data for a residual limb; (d) scan data for a positive model of the residual limb, or, (e) scan data for a positive model of an intended socket shape. In contrast, only about 30% of the points from the sampled splines were used in earlier approaches when aligning two residual limb shapes.

In addition, the present novel approach shows the data resulting from a scan of a socket in a useful format that facilitates analysis and determination of potential problems with the fit of the socket. Specifically, the data are processed to enable providing:

(1) a display of a shape difference map, for differences between the expected socket shape and the designed socket shape, which might be of immense help to a practitioner trying to understand how shape error affects the clinical fit of a socket.

(2) an indication of a socket volume difference between a measured socket shape and a designed socket shape; volume difference and maximum radii difference for each of seventeen critical regions of the socket (these regions are comparable to those used in commercial prosthetic CAD software packages (used to create the socket shape)), as well as regional volumes, as well as regions where a fabricator has consistently produced sockets that are in error relative to the designed socket shape; and, distances between feducial points (e.g., patellar tendon, tibial tuberosity, fibular head, and popliteal fossa).

Exemplary Logical Steps for Processing Data Resulting from Scanning Sockets

Figure 4:
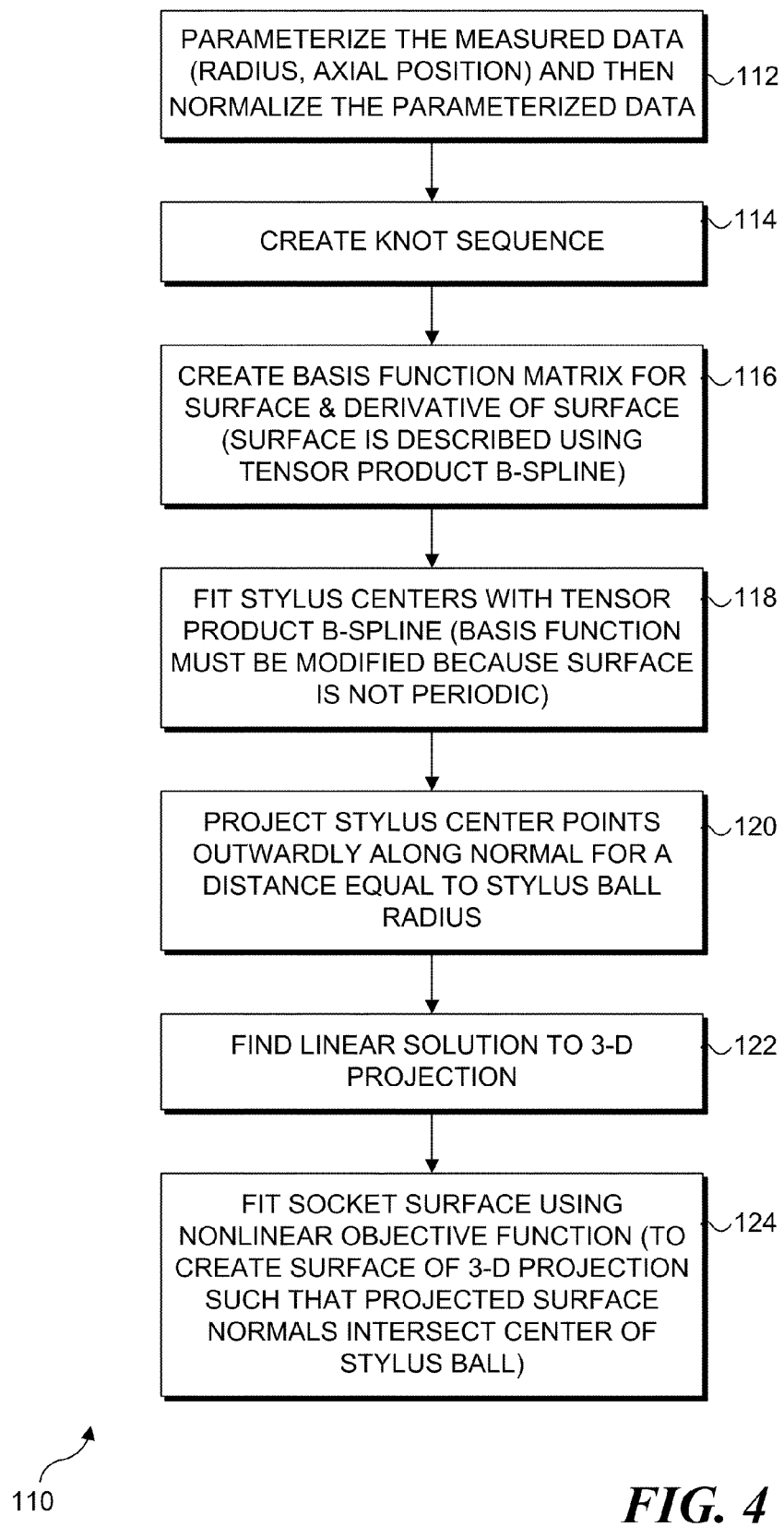
FIG. 4 is a flowchart illustrating exemplary logical steps for carrying out the three-dimensional (3-D) projection of digitizer data to accurately define the surface of an object such as an interior of a socket that is being scanned.

FIG. 4 illustrates a flowchart 110 showing exemplary detailed steps for creating the 3-D projections of the digitizer data as more generally discussed above. The procedure starts with a step 112, which normalizes the measured data produced by the digitizer at each measurement point, including the radius and axial position. Before collecting the data employed in this step, as noted above, it will be understood that the digitizer should be calibrated. The calibration ensures that the location of the stylus ball center is known at each measurement point. It will be appreciated that the height of the stylus ball (i.e., along the z or vertical axis) is not constant within a slice. After the calibration, the parameters u and v must be determined. The parameter u is based on the order in which the data are taken. For each slice, the data are numbered from 1 to 800 in this exemplary approach, where there are 800 points measured per slice. These data values are normalized so that they vary between 0 and 1. The v parameter is determined from the slices, where each slice of data taken is numbered from 1 up to the total number n of slices taken. The value for v is then also normalized to vary between 0 and 1. A step 114 provides for creating a knot sequence. In this step, the degrees for the u and v splines are set at 3. In the evaluation of the methods, there are 40 control points per row and 25 columns, for a total of 1000 control points. The knot sequences in the u and v directions are equally spaced, and the domain knots are 0 and 1. This relationship is shown for the u parameter below:

```
K_u=D_u+n_u-1 ( number of knots for theta splines)
KD_u=K_u-2*(n_u-1) (number of domain knots for theta splines)
step_u=(1-0)/(KD_u-1) (uniform step size)
knots_u=(0-(n_u-1)*step_u:step_u:1+(n_u-1)*step_u) (create knots)
knots_u=[knots_u(1,1),knots_u,knots_u(1,end)]
(Add knots for use in Matlab ™)
```

A step 116 provides for creating a basis function matrix for the surface and derivative of the surface (i.e., the surface is described using the tensor product B-spline). There is no spcol (B-spline collocation matrix) for tensor product splines; however, spcol in the Matlab™ software can still be used to develop the basis function matrix for the tensor product splines. The function spcol requires that the parameter input is non-decreasing, so the data must be manipulated. First, the data are sorted with respect to the u parameter value so that the data vary from 0 to 1. When calling the spcol function, two strings are added as the last two inputs; they are "sparse" and "noderiv." The string "sparse" makes the output of spcol a sparse matrix. Sparse matrices only store the location of nonzero valued elements. If the string "noderiv" is not sent, spcol will calculate the derivative at repeated parameter values. Once the data are sorted, the u component of the basis function can be found. Before the v component can be found, v must be sorted from 0 to 1. It is necessary to keep track of the indices from this sorting operation so the operation can be undone later. After finding the v-component of the basis function matrix, the data are unsorted, so that the data are only sorted with respect to v. The code for doing so follows:

```
data=[u,v,x,y,z];
[data_sort]=sortrows(data,[1]);
M_u=spcol(knots_u,k_u,u,"noderiv",'sparse");
[v_sort,v_inds]=sort(v,1);
M_v=spcol(knots_v,k_v,v_sort,"noderiv","sparse")'
(notice the transpose)
M_v(:,v_inds)=M_v (column operations on sparse matrices are faster).
```

Now M_u and M_v need to be put together into one basis function matrix, and this step can be done with the following line of code:

$$M = \text{repmat}(M\_u, 1, D\_v).*\text{reshape}(\text{repmat}(M\_v, 1, D\_u)', [], D\_u*D\_v).$$

The matrix M will have the same number of rows as data points and the same number of columns as there are control points, D_u*D_v. The rows are only sorted with respect to u. The first D_u columns of the first row of M are equal to M_u(1,:)*M_v(1,1), the second D_u columns of the first row are equal to M_u(1,:)*M_v(1,2), and so on.

The basis function matrices for the first derivatives are found in a similar fashion, and the code is shown below:

```
M_du=spcol(knots_u,k_u-1,u, "no","sp");
M_dv=spcol(knots_v,k_v-1,v_sort,"no,"'sp");
M_dv(:,v_inds)=M_dv;
Mdu=repmat(M_du,1,D_v).-
*reshape(repmat(M_v,1,D_u+1)',[ ],(D_u+1)*D_v);
Mdv=repmat(M_u,1,D_v+1).-
*reshape(repmat(M_dv,1,D_u)',[ ],D_u*(D_v+1)).
```

A step 118 then fits the stylus ball centers with the tensor product B-spline (the basis function must be modified to force the surface to periodic, which is necessary for the optimization). Linearity is assumed in order to develop a guess for the nonlinear solution. Since the basis function matrix has been developed, the solution can be found simply by:

$$d\_r = M\backslash \text{data\_sort}(:,3:5);$$

where d_r are the control points for the retracted surface. However, this surface will not be periodic with respect to u. The basis function is modified using the following code so that the least squares solution is periodic:

```
temp=M;
for i=0:D_v-1
temp(:,D_u*i+1:D_u*i+n_u)=temp(:,D_u*i+1:D_u*i+n_u)+temp(:,D_u*(i+1)-
    n_u+1:D_u*(i+1));
Mper(:,(D_u-n_u)*i+1:(D_u-n_u)*(i+1))=temp(:,(D_u)*i+1:D_u*(i+1)-n_u);
end
d_r=Mper\data_sort(:,3:5).
```

Because the last n columns were removed in the modification of M, the last n control points will have to be added back to the control points. The code to add the end of the x-component of the control points back is shown below:

```
dx=d_r(:,1);
dx=reshape(dx,[ ],D_v);
dx(D_u-n_u+1:D_u,:)=dx(1:n_u,:);
dx=reshape(dx,[ ],1).
```

Next, in a step 120, the stylus ball centers are projected outwardly along normals of the surface spline fit, to the socket surface, by a distance equal to the radius of the stylus ball. Fitting a tensor product spline to these points will be the guess for the nonlinear solution. The basis function matrices for the derivatives with respect to u and v have been calculated. The control points for the derivative must also be calculated. This step is done in the same way as for the curve case—by rows for the derivative with respect to u, and by columns for the derivative with respect to v. The derivative control points are calculated for the x-component below:

```
delta_u=knots_u(n_u+(1:D_u+1))-knots_u(1:D_u+1);
delta_u=reshape(repmat(delta_u',1,D_v),[ ],1);
dx_du=reshape(diff([zeros(1,D_v);reshape(dx,[ ],
    D_v);zeros(1,D_v)]),[ ],1)./delta_u;
delta_v=knots_v(n_v+(1:D_v+1))-knots_v(1:D_v+1);
delta_v=reshape(repmat(delta_v',1,D_u)',[ ],1);
dx_dv=reshape(diff([zeros(D_u,1),reshape(dx,[ ],D_v),
    zeros(D_u,1)],1,2),[ ],1)./delta_v.
```

This step is repeated for the y and z components of the control points. Then, the unit normal can be calculated at each point. The control points are projected outwardly along the normal by a distance equal to the radius of the ball and are fit to the socket surface. This step is shown below:

```
ds_du=[n_u*Mdu*dx_du,n_u*Mdu*dy_du,n_u*Mdu*dz_du];
ds_dv=[n_v*Mdv*dx_dv,n_v*Mdv*dy_dv,n_v*Mdv*dz_dv];
normals=cross(ds_du,ds_dv);
mag_normals=sqrt(normals(:,1).^2+normals(:,2).^2+
    normals(:,3).^2)*[1,1,1];
normals_unit=normals./mag_normals;
socket_data=data_sort(:,3:5)+r_sphere*normals_unit.
```

A linear solution to the 3-D projection is found in a step 122, in accord with:

$$d\_s = M per \backslash socket\_data(:,1:3);$$

In this solution the assumption is that the normals calculated at the surface fitted to the stylus ball centers will be the same as the normals calculated at the actual socket surface. This assumption is not necessarily true but may be very close. This solution will be used as the guess for the nonlinear solution.

Finally, in a step 124, the socket surface is fit using the nonlinear objective function (to create the surface of the 3-D projection such that the projected surface normals intersect the center of the stylus ball). Now that a very good guess for the solution has been generated, a Matlab™ optimization routine can be called. The function fminunc from the Matlab™ optimization toolbox is used to find the minimum error. This function is an unconstrained optimization routine. Instead of constraining the surface to be periodic through a constrained optimization, which is slower, the routine forces the solution to be periodic by only allowing fminunc to change the first D_u-n control points of each row. For example, for the case of n_u=3 and D_u=40, only the first 37 control points of each row are employed. Once inside the objective function, the first three control points can be added to the end of the row, bringing the total back to 40. The error is calculated and is returned to fminunc. In this way, when fminunc finds a solution, the error is minimized for the periodic spline. The code for calculating the error follows below:

```
fx=data(:,1)-M*dx+r*n_unit(:,1);
fy=data(:,2)-M*dy+r*n_unit(:,2);
fz=data(:,3)-M*dz+r*n_unit(:,3);
f=sum((fx).^2+(fy).^2+(fz).^2).
```

The data here are the stylus ball center locations, M is the basis function calculated earlier, (dx,dy,dz) are the control points, r is the stylus radius (1.5875 mm), and the n_unit variables are the unit normals at each point on the socket surface. The unit normals must be computed in the objective, since they are a function of the control points, but M is independent of the control points.

The gradient is also supplied to fminunc. Without supplying the gradient, the optimization takes around 30 minutes to take a step. With the gradient it can take a step in about a minute. The accuracy was checked with "derivativecheck" in fminunc, which compares the user supplied derivative to the derivative computed using finite differences. The max difference was small and on the order of $10^{-3}$.

A functional block diagram 400 showing exemplary steps for alignment of a surface 402 of a socket shape to a reference surface 404 of a reference shape is illustrated in FIG. 12. At the beginning of the computational procedure, if the dataset for the shape to be aligned is a collection of points, it is converted to a B-spline surface in a step 406 for the surface to be aligned and in a step 414 for the reference surface. This change is done not only to ensure that the surfaces contain all of the original data points, but also to later avoid a priori correspondence between points on the two surfaces.

The iterative closest point technique (ICP) is used in a step 408 to generate an initial guess of the transformation 412. A uniformly distributed relatively dense point set is generated for the surface to be aligned to the reference. The transformation that minimizes the sum of the squared distances between all points in the original shape and the closest points in the reference shape is determined. A least-squares, iterative, optimization strategy is carried out, translating and rotating each dataset relative to the reference in three dimensions until the sum of the squared distances between all points in the original shape and the closest points in the reference shape is minimized.

Then an optimization routine is carried out in a step 410 that is a weighted linear combination of maximized global similarity and maximized local shape similarity. The global similarity optimization is a minimization of the sum of the mean absolute distances between corresponding radii on the two point-sets. The local shape similarity optimization is a minimization of the difference in angle between corresponding surface normals on the two point-sets. The mean absolute distance is given a relative weight of 0.8 while the mean negative hyperbolic arc tangent of the surface-normal dot product is given a relative weight of 0.2. The maximum principal curvature and surface direction normals are computed at each point in the shape to be aligned, a straightforward computation since the shapes are stored as parameterized surfaces in terms of z and θ. The curvatures and tangents are computed using surface evaluations of the first- and second-order derivative surfaces. Next in step 410, the surface normals are obtained in a cross product computation. Since the angle between surface normals is close to zero for most point pairs, the negative hyperbolic arc tangent of the dot product is used for the computation in favor of the arc cosine.

Exemplary Scanning System

A functional block diagram 200 of an exemplary scanning system for digitizing the shape of a socket interior or the shape of another object is illustrated in FIG. 10. The system is controlled by a personal computer (PC) 202 that is provided with an AT6250-A™ servo controller and analog to digital (A/D) convertor card (available from Compumotor)—not separately shown. The servo controller card is coupled to a Gemini™ servodrive 1 (identified by reference number 204) and to a Gemini servodrive 2 (identified by reference number 212). The servodrive 1 drives an electric cylinder (with 8000 count encoder) 206 that controls the vertical position of a linear displacement transducer (LDT) 208. LDT 208 produces analog data signals indicative of the vertical position of the stylus ball that is scanning an object (i.e., position along the z-axis). These analog voltage data are converted to digital data that are input to PC 202, providing z-axis position feedback. Gemini servodrive 2 controls the servomotor with a 4000 count encoder 214, providing the rotational position control and sends the digital angle position directly to PC 202. A rotational variable differential transformer (RVDT) (210) is attached to the top of the cylinder piston and the four-bar linkage-mounting of the digitizer. The RVDT produces analog radial position voltage data signals that are converted to digital signals for input to PC 202, serving as an indication of the angular orientation of the front rod of the four-bar linkage, and thus, of angular orientation of the stylus and ball.

FIG. 11 schematically illustrates exemplary computing device 200 which includes a computer 364 suitable for implementing the present novel technique. Computer 364 may be a generally conventional personal computer (PC) such as a laptop, desktop computer, server, or other form of computing device or hardwire logic device. Computer 364 is coupled to a display 368, which is used for displaying text and graphics to the user, such as data showing a comparison of the shape digitized by scanning an object such as a prosthetic socket, with regard to: an electronic data file that defines a socket shape; the shape of another socket; the shape of a residual limb; or, the shape of a positive model for a socket.

Included within computer 364 is a processor 362. A memory 366 (with both read only memory (ROM) and random access memory (RAM)), a non-volatile storage 360 (such as a hard drive or other non-volatile data storage device) for storage of data and machine readable and executable instructions comprising modules and software programs, and digital data signals such as the data accumulated while an object such as a socket is being scanned and digitized, a network interface 352, and an optical drive 358 are coupled to processor 362 through a bus 354. Data that are stored can include the data that indicate the shape of a socket or another object that was scanned by the digitizer (or by another type of a data source), as well as electronic data that define a desired shape of the socket, or the shape of another socket, or data that define the shape of a residual limb or a positive model with which the scanned data are being compared. These data can alternatively be stored at a different location and accessed over a network 370, such as the Internet, or a local or wide area network, through network interface 352. Optical drive 358 can read a compact disk (CD) 356 (or other optical storage media, such as a digital video disk (DVD)) on which machine instructions are stored for implementing the present novel technique, as well as machine instructions comprising other software modules and programs that may be run by computer 364. The machine instructions are loaded into memory 366 before being executed by processor 362 to carry out the steps for implementing the present technique, and for other functions, such as solving the inverse problem to enable an electronic data file for a socket to be selected that will minimize the error between a desired design shape for the socket and the actual socket that is fabricated. The user can provide input to and/or control the processes that are implemented through keyboard/mouse 372, which is coupled to computer 364. A digitizer (or other device for determining a shape of a socket or other object) 374 is also connected to bus 354 for providing the data signals that indicate the shape determined by scanning the object. The scanned data can be stored as data on a non-volatile memory medium when an object is scanned and subsequently processed with computer 364 at a later time, or processed during the scanning of the object.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for using a computing device for assessing a prosthetic socket to determine an interior shape of the prosthetic socket and a deviation of the interior shape relative to a shape of a reference, comprising the steps of:
  (a) scanning an interior surface of the prosthetic socket to produce data indicative of a shape of the interior surface;
  (b) using the data, constructing an initial estimate for a B-spline surface that corresponds to the interior surface of the prosthetic socket;
  (c) optimizing the initial estimate of the B-spline surface to more accurately reconstruct a three-dimensional surface corresponding to the interior surface of the prosthetic socket;
  (d) comparing data for the three-dimensional surface defining the shape of the prosthetic socket, to data defining a shape of the reference, to determine deviations between the shape of the prosthetic socket and the reference; and (e) providing an indication of a magnitude and a location where the shape of the prosthetic socket deviates from the shape of the reference.

2. The method of claim 1, further comprising the step of optimizing the three-dimensional surface corresponding to interior surface of the prosthetic socket by projecting inwardly from points on the three-dimensional surface, to intersect with the scanning data, producing an optimized three-dimensional surface that more closely matches the interior surface of the prosthetic socket.

3. The method of claim 1, wherein the step of comparing the data for the three-dimensional surface of the prosthetic socket to the data defining the shape of the reference comprises the step of comparing the data for the three-dimensional surface of the prosthetic socket to data defining a shape of a reference that is selected from the group of references consisting of:
(a) another prosthetic socket;
(b) a residual limb that the prosthetic socket is designed to fit;
(c) a positive model of the residual limb that the prosthetic socket is designed to fit;
(d) a positive model of the intended socket shape; and
(e) electronically created shape data that represent a desired shape of the prosthetic socket.

4. The method of claim 1, wherein the step of comparing the data for the three-dimensional surface of the prosthetic socket to the data defining the shape of the reference comprises the step of comparing different regions of the three-dimensional surface of the prosthetic socket to corresponding regions of the reference.

5. The method of claim 4, wherein the step of comparing the data for the three-dimensional surface of the prosthetic socket to the data defining the shape of the reference further comprises the step of determining, for at least one region, both a mean absolute difference and a mean surface normal difference between the shape of the prosthetic socket that was determined and the shape of the reference.

6. The method of claim 4, further comprising the step of applying different weightings to the regions of the prosthetic socket that are compared to the corresponding regions of the reference, based on at least one of:
(a) anatomically related characteristics of the regions; and,
(b) computationally determined shape characteristics of the prosthetic socket.

7. The method of claim 1, further comprising the step of determining the interior surface of the prosthetic socket by constructing a B-spline surface, by minimizing a sum-of-squares Euclidian distance between measured points corresponding to the scanning data, and the interior surface being scanned.

8. The method of claim 7, wherein the step of constructing a B-spline surface corresponding to the interior surface of the prosthetic socket comprises the step of implementing a non-linear optimization to compute the control point locations so as to minimize a Euclidean sum-of-squares distance between the scanning data and the B-spline surface.

9. The method of claim 1, further comprising the steps of:
(a) compiling a database comprising a collection of electronic-shape file and socket-shape pairs that was established based on measurements of an interior shape of a plurality of prosthetic sockets produced by a specific socket manufacturing system or source, by determining a measured shape of each of the plurality of prosthetic sockets to a corresponding electronic-shape-file used to produce the prosthetic socket;
(b) determining a desired prosthetic socket shape for a specific residual limb of a patient using a computer program and extracting shape features of interest for achieving a fit to the specific residual limb from the desired prosthetic socket shape;
(c) selecting an electronic-shape file and socket-shape pair from the database based on the socket-shape that appears to most closely match the desired prosthetic socket shape;
(d) simulating fabrication of a prosthetic socket as defined by the electronic-shape file of the pair that was selected, using a transfer function that characterizes changes in key features of the prosthetic socket produced using the electronic-shape file of the pair that was selected, said transfer function producing a predicted manufactured shape of the prosthetic socket that might thus be fabricated using said electronic-shape file;
(e) comparing the predicted manufactured shape of the prosthetic socket that might thus be fabricated with the shape features of interest that were extracted from the desired prosthetic socket shape for the specific residual limb, and determining if any errors that are detected are within predetermined tolerances, and if so, using the electronic-shape file that was selected to fabricate a prosthetic socket to fit the residual limb; and conversely,
(f) if any errors detected are not within the predetermined tolerances, adjusting a plurality of shape control points in the electronic-shape file that was selected, and repeating the steps of simulating and comparing using the electronic-shape file that was selected and modified, and if necessary, iteratively adjusting the plurality of shape control points and carrying out the steps of simulating and comparing using the electronic-shape file as last modified, until results of the step of comparing are within the predetermined tolerances, so that electronic-shape file that was selected and as last modified is then used for fabricating the prosthetic socket to fit the residual limb.

10. The method of claim 9, further comprising the step of adding to the database a new pair, wherein the new pair comprises the electronic-shape file as last modified and a shape of the prosthetic socket that was actually fabricated using the electronic-shape file as last modified.

11. The method of claim 9, wherein the step of comparing the predicted manufactured shape of the prosthetic socket that might thus be fabricated with shape features of interest that were extracted from the desired prosthetic socket shape comprises the step of comparing only specific regions of the predicted manufactured shape and corresponding regions of the shape extracted from the desired prosthetic socket shape that are weighted according to a likely impact of each region on comfort, tissue health, or stability, when a fabricated prosthetic socket shape is used on the residual limb, the specific regions comprising the features of interest.

12. The method of claim 1, wherein the step of providing an indication of a magnitude and a location where the shape of the prosthetic socket deviates from the shape of the reference comprises the step of displaying a shape difference map between the shape of the interior of the prosthetic socket and the shape of the reference.

13. The method of claim 1, wherein the step of providing an indication of a magnitude and a location where the shape of the prosthetic socket deviates from the shape of the reference comprises the step of indicating at least one of:

(a) a volume difference between the prosthetic socket and the reference;
(b) regional volume differences between the prosthetic socket and the reference;
(c) maximum radii differences for each of a plurality of different regions of the prosthetic socket;
(d) regions of where errors between the shape of the prosthetic socket and the shape of the reference have consistently been detected; and
(e) distances between feducial points in the shape of the prosthetic socket and corresponding distances between feducial points on the shape of the reference.

14. A system for assessing a prosthetic socket to determine an interior shape of the prosthetic socket and a deviation of the interior shape relative to a shape of a reference, comprising:
(a) a scanner having a plurality of encoders configured to produce signals indicative of the interior shape of the prosthetic socket; and
(b) a computing device that is coupled to the scanner to receive the signals from the encoders, the computing device including a memory in which machine executable instructions are stored, and a processor that is coupled to the memory, the processor executing the machine instructions to implement a plurality of functions, including:
(i) scanning an interior surface of the prosthetic socket to produce data indicative of a shape of the interior surface;
(ii) using the data, constructing an initial estimate for a B-spline surface that corresponds to the interior surface of the prosthetic socket;
(iii) optimizing the initial estimate of the B-spline surface to more accurately reconstruct a three-dimensional surface corresponding to the interior surface of the prosthetic socket;
(iv) comparing data for the three-dimensional surface defining the shape of the prosthetic socket, to data defining a shape of the reference, to determine deviations between the shape of the prosthetic socket and the reference; and
(v) providing an indication of a magnitude and a location where the shape of the prosthetic socket deviates from the shape of the reference.

15. The system of claim 14, wherein execution of the machine instructions further causes the processor to optimize the three-dimensional surface corresponding to interior surface of the prosthetic socket by projecting inwardly from points on the three dimensional surface, to intersect with the scanning data, producing an optimized three-dimensional surface that more closely matches the interior surface of the prosthetic socket.

16. The system of claim 14, wherein execution of the machine instructions further causes the processor to compare data for the three-dimensional surface of the prosthetic socket to data defining a shape of a reference that is selected from the group of references consisting of:
(a) another prosthetic socket;
(b) a residual limb that the prosthetic socket is designed to fit;
(c) a positive model of the desired socket shape;
(d) a positive model of the residual limb that the prosthetic socket is designed to fit; and
(e) electronically created shape data that represent a desired shape of the prosthetic socket.

17. The system claim 14, wherein execution of the machine instructions further causes the processor to compare different regions of the three-dimensional surface of the prosthetic socket to corresponding regions of the reference.

18. The system of claim 17, wherein execution of the machine instructions further causes the processor to determine, for at least one region, both a mean absolute difference and a mean surface normal difference between the shape of the prosthetic socket that was determined and the shape of the reference.

19. The system of claim 17, wherein execution of the machine instructions further causes the processor to apply different weightings to the regions of the prosthetic socket that are compared to the corresponding regions of the reference, based on at least one of:
(a) anatomically related characteristics of the regions; and,
(b) computationally determined shape characteristics of the prosthetic socket.

20. The system of claim 14, wherein execution of the machine instructions further causes the processor to construct a B-spline surface by minimizing a sum-of squares Euclidian distance between measured points corresponding to the scanning data, and the interior surface being scanned.

21. The system of claim 20, wherein execution of the machine instructions further causes the processor to:
(a) compile a database comprising a collection of electronic-shape file and socket-shape pairs that was established based on measurements of an interior shape of a plurality of prosthetic sockets produced by a specific socket manufacturing system or source, by determining a measured shape of each of the plurality of prosthetic sockets to a corresponding electronic-shape-file used to produce the prosthetic socket;
(b) determine a desired prosthetic socket shape for a specific residual limb of a patient using a computer program and extracting shape features of interest for achieving a fit to the specific residual limb from the desired prosthetic socket shape;
(c) enable a practitioner to select an electronic-shape file and socketshape pair from the database based on the socket-shape that appears to most closely match the desired prosthetic socket shape;
(d) simulate fabrication of a prosthetic socket as defined by the electronic-shape file of the pair that was selected, using a transfer function that characterizes changes in key features of the prosthetic socket produced using the electronic-shape file of the pair that was selected, said transfer function producing a predicted manufactured shape of the prosthetic socket that might thus be fabricated using said electronic-shape file;
(e) compare the predicted manufactured shape of the prosthetic socket that might thus be fabricated with the shape features of interest that were extracted from the desired prosthetic socket shape for the specific residual limb, and determine if any errors that are detected are within predetermined tolerances, and if so, indicate that the electronic-shape file that was selected can be used to fabricate a prosthetic socket to fit the residual limb; and conversely,
(f) if any errors detected are not within the predetermined tolerances, adjust a plurality of shape control points in the electronic-shape file that was selected, and repeat the functions of simulating and comparing using the electronic-shape file that was selected and modified, and if necessary, iteratively adjust the plurality of shape control points and carry out the functions of simulating and comparing using the electronic-shape file as last modified, until results of the function of comparing are within the predetermined tolerances, so that the electronic-shape file that was selected as last modified can be identified as suitable for fabricating the prosthetic socket to fit the residual limb.

22. The system of claim 21, wherein execution of the machine instructions further causes the processor to add a new pair to the database, wherein the new pair comprises the electronic-shape file as last modified and a shape of the prosthetic socket that was actually fabricated using the electronic-shape file as last modified.

23. The system of claim 21, wherein execution of the machine instructions further causes the processor to compare only specific regions of the predicted manufactured shape and corresponding regions of the shape extracted from the desired prosthetic socket shape that are weighted according to a likely impact of each region on at least one of comfort, tissue health, and stability, when a fabricated prosthetic socket shape is used on the residual limb, the specific regions comprising the features of interest.

24. The system of claim 14, wherein the computing device includes a display, and wherein execution of the machine instructions further causes the processor to graphically portray a shape difference map between the shape of the interior of the prosthetic socket and the shape of the reference on the display.

25. The system of claim 14, wherein the computing device further includes a display, and wherein execution of the machine instructions further causes the processor to indicate on the display at least one of:
   (a) a volume difference between the prosthetic socket and the reference;
   (b) regional volume differences between the prosthetic socket and the reference;
   (c) maximum radii differences for each of a plurality of different regions of the prosthetic socket;
   (d) regions of consistent error between the shape of the prosthetic socket and the shape of the reference; and
   (e) distances between feducial points in the shape of the prosthetic socket and corresponding distances between feducial points on the shape of the reference.

* * * * *